United States Patent
Kehler et al.

(10) Patent No.: US 7,618,967 B2
(45) Date of Patent: Nov. 17, 2009

(54) INDANE COMPOUNDS

(75) Inventors: Jan Kehler, Lyngby (DK); Karsten Juhl, Greve (DK); Ask Püschl, Frederiksberg (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 113 days.

(21) Appl. No.: 11/847,369

(22) Filed: Aug. 30, 2007

(65) Prior Publication Data

US 2008/0058329 A1 Mar. 6, 2008

Related U.S. Application Data

(60) Provisional application No. 60/841,942, filed on Aug. 31, 2006, provisional application No. 60/938,945, filed on May 18, 2007.

(51) Int. Cl.
| | |
|---|---|
| *A61K 31/5377* | (2006.01) |
| *A61K 31/404* | (2006.01) |
| *A61P 13/02* | (2006.01) |
| *A61P 25/16* | (2006.01) |
| *A61P 25/24* | (2006.01) |
| *A61P 25/34* | (2006.01) |
| *C07D 209/04* | (2006.01) |
| *C07D 295/00* | (2006.01) |
| *C07D 221/00* | (2006.01) |
| *A61P 43/00* | (2006.01) |
| *A61P 25/28* | (2006.01) |
| *A61K 31/445* | (2006.01) |

(52) U.S. Cl. .................... 514/235.2; 514/323; 514/414; 514/415; 514/210.18; 514/317; 514/231.2; 544/143; 546/201; 548/950; 548/518; 548/465; 548/503

(58) Field of Classification Search ................. 514/414, 514/415, 422, 210.18, 317, 323, 218, 231.1; 544/143; 546/201; 548/518, 469, 950
See application file for complete search history.

(56) References Cited

U.S. PATENT DOCUMENTS

| 4,873,344 | A | 10/1989 | Bogeso et al. |
|---|---|---|---|
| 5,559,134 | A | 9/1996 | Buchmann et al. |
| 5,773,463 | A | 6/1998 | Harling et al. |
| 6,268,535 | B1 | 7/2001 | Moussa et al. |
| 2005/0085530 | A1 | 4/2005 | Bogeso et al. |

FOREIGN PATENT DOCUMENTS

| EP | 0 271 225 A2 | 6/1988 |
|---|---|---|
| WO | WO 92/10192 A1 | 6/1992 |
| WO | WO 93/22293 A1 | 11/1993 |
| WO | WO 94/04522 A1 | 3/1994 |
| WO | WO 95/04027 A1 | 2/1995 |
| WO | WO 95/04028 A1 | 2/1995 |
| WO | WO 95/18617 A1 | 7/1995 |
| WO | WO 95/29907 | 11/1995 |
| WO | WO 96/06840 | 3/1996 |
| WO | WO 98/55447 A1 | 12/1998 |
| WO | WO 99/35119 | 7/1999 |
| WO | WO 01/10842 A2 | 2/2001 |
| WO | WO 2003/055873 A1 | 7/2003 |
| WO | WO 2004/026237 A2 | 4/2004 |
| WO | WO 2005/016901 A1 | 2/2005 |
| WO | WO 2005/061455 A1 | 7/2005 |
| WO | WO 2005/092854 A1 | 10/2005 |
| WO | WO 2006/086984 A1 | 8/2006 |
| WO | WO 2007/073503 A2 | 6/2007 |

OTHER PUBLICATIONS

Klaus P. Bogeso et al.: "3-phenyl-1-indanamines. Potential Antidepressant Activity and Potent Inhibition of Dopamine, Norepinephrine, and Serotonin Uptake", J. Med. Chem., vol. 28, No. 12, 1985, p. 1817-1828.
Clar, E., et al., "New Benzenogenic Diene Syntheses", Tetrahedron, 1974, 30:3293-3298.
Durani, N., et al., "Structure-Activity Relationship Of Antiestrogens: A Study Using Triarylbutenone, Benzofuran, and Triarylfuran Analogues as Models for Triarylethylenes and Triarylpropenones", J. Med. Chem., 1989, 32(8):1700-1707.
Ecker, G., et al., "Structure-Activity Relationship Studies on Benzofuran Analogs of Propafenone-Type Modulators of Tumor Cell Multidrug Resistance", J. Med. Chem., 1996, 39(24):4767-4774.
Johnston, K. M., and Shotter, R. G., "Friedel-Crafts Cyclisation—IV. Intramolecular vs Intermolecular Acylation with beta-Aryl Derivatives of Propionyl Chloride In Aromatic Substrates", Tetrahedron, 1974, 30:4059-4064.
Khan, A., et al., "Venlafaxine in Depressed Outpatients", Psychopharmacology Bulletin, 1991, 27(2):141-144.
Smonou, T. and Orfanopoulos, M., "Convenient Synthetic Sequence for the Preparation of Indanones", Synthetic Communications, 1990, 20(9):1387-1397.
Sommer, M. B., et al., "Application of (2-Cyanoaryl)arylacetonitriles in Cyclization and Annulation Reactions. Preparation Of 3-Arylindans, 4-Aryl-3,4-dihydronaphthalenes, 4-Arylisoquinolines, 1-Aminonaphthalenes, and Heterocyclic Analogues", J. Org. Chem., 1990, 55(16):4822-4827.
Wong, D.T., "Duloxetine (LY 248686): an inhibitor of serotonin and noradrenaline uptake and an antidepressant drug candidate", Exp. Opin. Invest. Drugs, 1998, 7(10):1691-1699.
Zaidlewicz, M., et al., "Asymmetric synthesis of (S)-bufaralol and a propafenone analogue", Tetrahedron: Asymmetry, 2003, 14:1659-1664.

*Primary Examiner*—Yong Chu
(74) *Attorney, Agent, or Firm*—Stephen G. Kalinchak

(57) ABSTRACT

The invention provides novel indane compounds which are useful in the treatment of affective disorders, pain disorders, attention deficit hyperactivity disorder (ADHD), cognitive disorders, substance abuse, smoking cessation and stress urinary incontinence.

22 Claims, No Drawings

INDANE COMPOUNDS

This application claims the benefit of priority of U.S. Provisional Application No. 60/841,942, filed Aug. 31, 2006 and U.S. Provisional Application No. 60/938,945, filed May 18, 2007, the contents of which are hereby incorporated by reference into the subject application.

FIELD OF THE INVENTION

The invention provides novel indane compounds which are useful in the treatment of depression, anxiety and other CNS disorders.

BACKGROUND OF THE INVENTION

All currently available antidepressants can be classified in 3 classes:
1) monoamine oxidase inhibitors (MAOIs),
2) biogenic amine neurotransmitter [serotonin (5-HT), norepinephrine (NE) and dopamine (DA)] transporter reuptake blockers, and
3) modulators, especially blockers of one or more of the 5-HT and/or NE receptors.

Since depression is associated with a relative deficiency of the biogenic amines, the use of 5-HT and/or NE-receptor blockers (i.e. 5-HT and or NE-antagonist's) has not proven very successful in the treatment of depression and anxiety and the preferred and currently most efficient treatments are based on the enhancement of 5-HT and/or NE neurotransmission by blocking their reuptake back from the synaptic cleft (Slattery, D. A. et al., "The evolution of antidepressant mechanisms", *fundamental and Clinical pharmacology*, 2004, 18, 1-21; Schloss, P. et al, "new insights into the mechanism of antidepressant therapy", *Pharmacology and therapeutics*, 2004, 102, 47-60).

Selective serotonin reuptake inhibitors (hereinafter referred to as SSRIs) have become first choice therapeutics in the treatment of depression, certain forms of anxiety and social phobias, because they generally are effective, well tolerated and have a favourable safety profile compared to the classic tricyclic antidepressants. Drugs claimed to be SSRIs are for example flouxetine, sertraline and paroxetine.

However, clinical studies on depression indicate that non-response to the known SSRIs is substantial, up to 30%. Another, often neglected, factor in antidepressant treatment is the fact that there is generally a delay in therapeutic effect of the SSRIs. Sometimes symptoms even worsen during the first weeks of treatment. Furthermore, sexual dysfunction is generally a side effect common to SSRIs. Accordingly, there is a desire for the development of compounds capable of improving the treatment of depression and other serotonin related diseases.

A newer strategy has been the development of dual re-uptake inhibitors, e.g., the combined effect of 5-HT reuptake inhibition and NE (norepinephrine is also named noradrenaline, NA) reuptake inhibition on depression is explored in clinical studies of compounds such as Duloxetine (Wong, "Duloxetine (LY-248686): an inhibitor of serotonin and noradrenaline uptake and an antidepressant drug candidate", *Expert Opinion on Investigational Drugs*, 1998, 7, 10, 1691-1699) and Venlafaxine (Khan-A et al, 30 "Venlafaxine in depressed outpatients", *Psychopharmacology Bulletin*, 1991, 27, 141-144). Compounds having such dual effect are also named SNRIs, "serotonin and noradrenaline reuptake inhibitors", or NSRIs, "noradrenaline and serotonin reuptake inhibitors".

Since treatment with the selective NE reuptake inhibitor reboxetine has been shown to stimulate 5-HT neurons and mediate the release of 5-HT in the brain (Svensson, T. et al, *J. Neural. Transmission*, 2004, 111, 127) there might be a synergistic advantage using SNRI's in the treatment of depression or anxiety.

The use of SNRI's has been shown in clinical studies to have a beneficial effect on pain (e.g. Fibromyalgia syndrome, overall pain, back pain, shoulder pain, headache, pain while awake and during daily activities) and especially pain associated with depression (Berk, M. *Expert Rev. Neurotherapeutics* 2003, 3, 47-451; Fishbain, D. A., et al. "Evidence-based data from animal and human experimental studies on pain relief with antidepressants: A structured review" Pain Medicine 2000 1:310-316).

SNRI's have also been shown in clinical studies to have a beneficial effect in attention deficit hyperactivity disorder (ADHD) (N. M. Mukaddes; Venlafaxine in attention deficit hyperactivity disorder, European Neuropsychopharmacology, Volume 12, Supplement 3, October 2002, Page 421).

Furthermore, SNRI's have been shown to be effective for the treatment of stress urinary incontinence (Dmochowski R. R. et al. "Duloxetine versus placebo for the treatment of North American women with stress urinary incontinence", Journal of Urology 2003, 170:4, 1259-1263.)

Naranjo, C. et al. "The role of the brain reward system in depression" *Prog. Neuro-Psychopharmacol. Biol. Psychiatry* 2001, 25, 781-823 discloses clinical and preclinical findings of links between lack of extra cellular dopamine in the meso-corticolimbic system and anhedonia, which is one of the main symptoms of depression.

Several studies suggest that serotonin and dopamine neurotransmission dysfunction contribute to the pathophysiology of several neuropsychiatric disorders, which include depression, schizophrenia and drug abuse (Fibiger, H. C., et al., "In Depression and Mania: from neurobiology to treatment" Raven Press, New York 1995, pp. 1-17; Roth, B. L., et al., *J. Pharmacol. Exp. Ther.* 1992, 260, pp. 1361-1365; Koob, G. F, et al., *Trends Pharmacol. Sci.* 1992, 13, pp. 177-184; Brown, A. S., et al., *J. Neural. Trans.* 1993, 91, pp. 75-109). Esposito, E., et al., "Serotonin-Dopamine Interaction as focus of Novel Antidepressant Drugs" *Curr. Drug Targets* 2006, 7, pp 177-185, suggests that drugs acting on the 5-HT system (e.g. SSRI's and 5-HT$_{2C}$ receptor antagonist) exert their antidepressant action by enhancing dopaminergic transmission in the mesolimbic system, and the use of such drugs, which influence the mesolimbic DA transmission might be important and useful in the search of new antidepressants for the treatment of depression.

Furthermore, Axford L. et al. describe the development of triple 5-HT, NE and DA re-uptake inhibitors for treatment of depression. (2003, *Bioorganic & Medical Chemistry Letters*, 13, 3277-3280: "Bicyclo[2.2.1.]heptanes as novel triple re-uptake inhibitors for the treatment of depression"). Wellbutrin (bupropion) which has DA re-uptake activity in vitro and in vivo, show antidepressant efficacy. Other combination studies have indicated that addition of some affininity at the DA uptake site may have some clinical benefit (Nelson, J. C. J. *Clin. Psychiatry* 1998, 59, 65; Masand, P. S. et al. *Depression Anxiety* 1998, 7, 89; Bodkin, J. A et al. *J. Clin. Psychiatry* 1997, 58, 137).

The combination of an SSRI and a norepinephrine and dopamine reuptake inhibitor, has been shown to have better efficacy in SSRI-non-responders (Lam R. W. et al. "Citalopram and Bupropion-SR: Combining Versus Switching in Patients With Treatment-Resistant Depression." *J. Clin. Psychiatry* 2004, 65, 337-340).

There is clinical evidence suggesting that the combination of an SSRI and a norepinephrine and dopamine reuptake inhibitor induces less sexual dysfunction, than treatment with SSRI's alone (Kennedy S. H. et al. "Combining Bupropion SR With Venlafaxine, Paroxetine, or Duloxetine: A Preliminary Report on Pharmacokinetic, Therapeutic, and Sexual Dysfunction Effects" *J. Clin. Psychiatry* 2002, 63, 181-186).

The development of triple serotonin, norepinephrine and dopamine re-uptake inhibitors are currently the focus of many pharmaceutical companies, for their improved efficacy and reduced delay of action (Millan, M. J., et al. "Multi-target strategies for the improvement of depressive states: Conceptual Foundations And Neuronal Substrates, Drug Discovery And Therapeutic Application." *Pharmacology & Therapeutics.* 110 (2006), 135-370).

The present invention provides novel indane compounds which are inhibitors of serotonin, norepinephrine and dopamine re-uptake. The compounds of the invention are therefore useful in the treatment of affective disorders, pain disorders, attention deficit hyperactivity disorder (ADHD), substance abuse, cognitive deficits and stress urinary incontinence.

SUMMARY OF THE INVENTION

An object of the invention is to provide compounds of the Formulas I-X, as defined below, which are inhibitors of serotonin, norepinephrine and dopamine re-uptake. The compounds of the invention are therefore useful in the treatment of affective disorders, pain disorders, attention deficit hyperactivity disorder (ADHD), cognitive disorders, substance abuse, smoking cessation and stress urinary incontinence.

In one embodiment, the compounds of the Formulas I-X, as defined below, are useful in the treatment of affective disorders. To further illustrate but without limiting the invention, the affective disorder to be treated is selected from the group consisting of depressive disorders and anxiety disorders.

In one embodiment, the depressive disorders to be treated are selected from the group consisting of major depressive disorder, melancholia, postnatal depression, dysthymia and depression associated with bipolar disorder, Alzheimer's, psychosis or Parkinson's disease. To further illustrate without limiting the invention, an embodiment of the invention concerns the treatment of depression associated with bipolar disorder; another embodiment concerns the treatment of depression associated with Alzheimer's; another embodiment concerns the treatment of depression associated with psychosis; and another embodiment concerns the treatment of depression associated with Parkinson's disease.

In another embodiment, the anxiety disorders to be treated are selected from the group consisting of general anxiety disorder, social anxiety disorder, post traumatic stress disorder, obsessive compulsive disorder, panic disorder, panic attacks, specific phobias, social phobia and agoraphobia.

In another embodiment, the compounds of the invention are useful in the treatment of pain disorders. To further illustrate but without limiting the invention, the pain disorder to be treated is selected from the group consisting of fibromyaglia syndrome (FMS), overall pain, back pain, shoulder pain, headache as well as pain while awake and during daily activities. To further illustrate without limiting the invention, an embodiment of the invention concerns the treatment of fibromyalgia syndrome (FMS); another embodiment concerns the treatment of overall pain; another embodiment concerns the treatment of back pain; another embodiment concerns the treatment of shoulder pain; another embodiment concerns the treatment of headache; and another embodiment concerns the treatment of pain while awake and during daily activities.

In another embodiment, the compounds of the invention are useful in the treatment of attention deficit hyperactivity disorder (ADHD) and other cognitive disorders.

In another embodiment, the compounds of the invention are useful in the treatment of both substance abuse and smoking cessation.

In another embodiment, the compounds of the invention are useful in the treatment of stress urinary incontinence.

In a second aspect, the present invention relates to the use of a compound of the Formulas I-X, as defined below, for the manufacture of a medicament useful for the treatment of affective disorders, pain disorders, attention deficit hyperactivity disorder (ADHD), cognitive disorders, substance abuse, smoking cessation and stress urinary incontinence.

In one embodiment, the present invention relates to the use of a compound of the Formulas I-X, as defined below, for the manufacture of a medicament useful for the treatment of affective disorders. To further illustrate without limiting the invention, the affective disorder to be treated is selected from the group consisting of depressive disorders and anxiety disorders.

In one embodiment, the depressive disorders to be treated are selected from the group consisting of major depressive disorder, melancholia, postnatal depression, dysthymia and depression associated with bipolar disorder, Alzheimer's, psychosis or Parkinson's disease. To further illustrate without limiting the invention, an embodiment of the invention concerns the treatment of depression associated with bipolar disorder; another embodiment concerns the treatment of depression associated with Alzheimer's; another embodiment concerns the treatment of depression associated with psychosis; and another embodiment concerns the treatment of depression associated with Parkinson's disease.

In another embodiment, the anxiety disorders to be treated are selected from the group consisting of general anxiety disorder, social anxiety disorder, post traumatic stress disorder, obsessive compulsive disorder, panic disorder, panic attacks, specific phobias, social phobia and agoraphobia.

In another embodiment, the invention relates to the use of a compound of Formulas I-X, as defined below, for the manufacture of a medicament useful for the treatment of pain disorders. To further illustrate without limiting the invention, the pain disorder to be treated is selected from the group consisting of fibromyaglia syndrome (FMS), overall pain, back pain, shoulder pain, headache as well as pain while awake and during daily activities.

In another embodiment, the invention relates to the use of a compound of Formulas I-X, as defined below, for the manufacture of a medicament useful for the treatment of attention deficit hyperactivity disorder (ADHD) and other cognitive disorders.

In another embodiment, the invention relates to the use of a compound of Formulas I-X, as defined below, for the manufacture of a medicament useful for the treatment of substance abuse and smoking cessation.

In another embodiment, the invention relates to the use of a compound of Formulas I-X, as defined below, for the manufacture of a medicament useful for the treatment of stress urinary incontinence.

In a third aspect, the present invention relates to a pharmaceutical composition comprising a compound of Formulas I-X, as defined below, in a therapeutically effective amount together with one or more pharmaceutically acceptable carriers or diluents.

In a fourth aspect, the present invention relates to treating a disease, where the inhibition of serotonin, and/or norepinephrine and/or dopamine re-uptake is implicated, comprising administration of a therapeutically effective amount of a compound of the Formulas I-X, as defined below, to a mammal including humans.

In a fifth aspect, the present invention relates to a method of treating affective disorders, pain disorders, attention deficit hyperactivity disorder (ADHD), cognitive disorders, substance abuse, smoking cessation and stress urinary incontinence, comprising the administration of a therapeutically effective amount of a compound of the Formula I-X, as defined below, to a mammal including humans.

In one embodiment, the present invention relates to a method of treating affective disorders, comprising the administration of a therapeutically effective amount of a compound of the Formula I-X, as defined below, to a mammal including humans. To further illustrate without limiting the invention, the affective disorder to be treated is selected from the group consisting of depressive disorders and anxiety disorders.

In one embodiment, the depressive disorders to be treated are selected from the group consisting of major depressive disorder, melancholia, postnatal depression, dysthymia and depression associated with bipolar disorder, Alzheimer's, psychosis or Parkinson's disease. To further illustrate without limiting the invention, an embodiment of the invention concerns the treatment of depression associated with bipolar disorder; another embodiment concerns the treatment of depression associated with Alzheimer's; another embodiment concerns the treatment of depression associated with psychosis; and another embodiment concerns the treatment of depression associated with Parkinson's disease.

In another embodiment, the anxiety disorders to be treated are selected from the group consisting of general anxiety disorder, social anxiety disorder, post traumatic stress disorder, obsessive compulsive disorder, panic disorder, panic attacks, specific phobias, social phobia and agoraphobia.

In further embodiment, the depressive disorder to be treated is selected from the group consisting of major depressive disorder, melancholia, postnatal depression, dysthymia and depression associated with bipolar disorder, Alzheimer's, psychosis or Parkinson's disease. To further illustrate without limiting the invention, an embodiment of the invention concerns the treatment of depression associated with bipolar disorder; another embodiment concerns the treatment of depression associated with Alzheimer's; another embodiment concerns the treatment of depression associated with psychosis; another embodiment concerns the treatment of depression associated with Parkinson's disease.

In even a further embodiment, the present invention relates to a method of treating anxiety disorders, comprising the administration of a therapeutically effective amount of a compound of the Formula I-X, as defined below, to a mammal including humans.

In further embodiment, the anxiety disorders to be treated are selected from the group consisting of general anxiety disorder, social anxiety disorder, post traumatic stress disorder, obsessive compulsive disorder, panic disorder, panic attacks, specific phobias, social phobia and agoraphobia.

In another embodiment, the present invention relates to a method of treating pain disorders, comprising the administration of a therapeutically effective amount of a compound of the Formula I-X, as defined below, to a mammal including humans. To further illustrate without limiting the invention, the pain disorder to be treated is selected from the group consisting of fibromyaglia syndrome (FMS), overall pain, back pain, shoulder pain, headache as well as pain while awake and during daily activities.

In another embodiment, the present invention relates to a method of treating attention deficit hyperactivity disorder (ADHD) and other cognitive disorders, comprising the administration of a therapeutically effective amount of a compound of the Formula I-X, as defined below, to a mammal including humans.

In another embodiment, the present invention relates to a method of treating substance abuse and smoking cessation, comprising the administration of a therapeutically effective amount of a compound of the Formula I-X, as defined below, to a mammal including humans.

In another embodiment, the present invention relates to a method of treating stress urinary incontinence, comprising the administration of a therapeutically effective amount of a compound of the Formula I-X, as defined below, to a mammal including humans.

DETAILED DESCRIPTION OF THE INVENTION

The present invention provides compounds that are represented by the Formula I

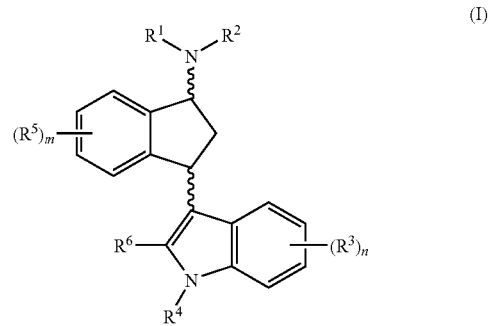

(I)

Wherein each $R^1$ and $R^2$ are independently hydrogen, $C_1$-$C_8$-straight or branched alkyl or $C_3$-$C_8$-cycloalkyl; or wherein $R^1$ and $R^2$ and the nitrogen to which they are attached form azetidine, piperidine, pyrrolidine, azapane or morpholine;

Wherein each $R^3$ is independently hydrogen, $C_1$-$C_8$-straight or branched alkyl, $C_1$-$C_5$-alkoxy, $C_1$-$C_8$-straight or branched polyfluoroalkyl, halogen, cyano, hydroxyl, tetrazole-optionally substituted with methyl, or amino; or wherein two $R^3$ groups on adjacent carbons combine together to form a methylenedioxy linker;

wherein $R^4$ is hydrogen, $C_1$-$C_8$-straight or branched alkyl or $C_3$-$C_8$-cycloalkyl;

wherein each $R^5$ is hydrogen, halogen, $C_1$-$C_5$-alkoxy, $C_1$-$C_8$-straight or branched alkyl, $C_1$-$C_8$-straight or branched polyfluoroalkyl, cyano, or hydroxyl;

m is an integer from 1 to 4 inclusive;

n is an integer from 1 to 4 inclusive; and wherein $R^6$ is hydrogen, $C_1$-$C_8$-straight or branched alkyl or phenyl;

or pharmaceutically acceptable salts thereof.

In one embodiment the compounds represented by the Formula I are the pure enantiomers, diasteromers and mixtures thereof.

In another embodiment the compound represented by the Formula I is the cis isomer of Formula II and III; In another embodiment the compound represented by the Formula I is the trans isomer of Formula IV and V.

In another embodiment, the present invention relates to compounds of the Formula II-V

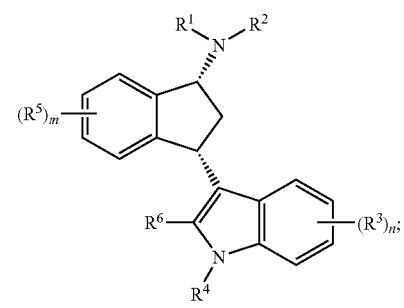

(II)

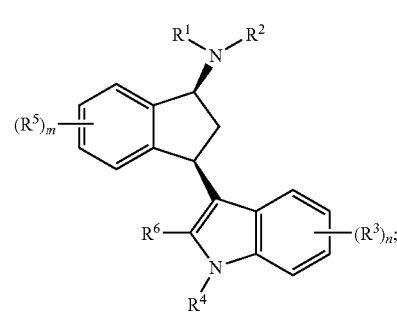

(III)

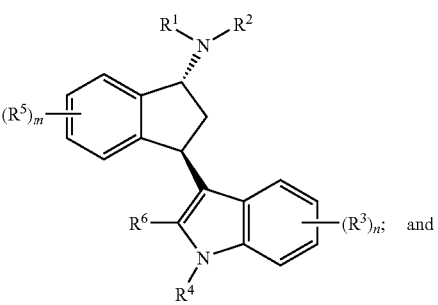

(IV)

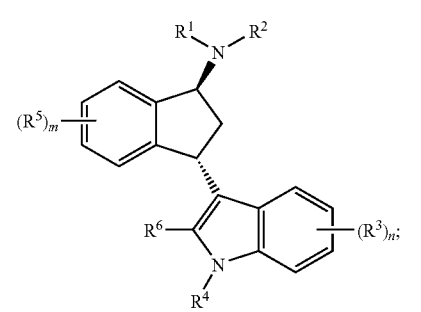

(V)

Wherein $R^1$, $R^2$, $R^3$, $R^4$, $R^5$, $R^6$, m and n are as defined above.

In one embodiment $R^1$ is hydrogen. In one embodiment $R^2$ is methyl. In one embodiment $R^4$ is hydrogen. In one embodiment $R^3$ is selected form the group consisting of hydrogen, halogen, and methoxy. In one embodiment $R^3$ is a hydrogen or halogen. In one embodiment the halogen is fluorine or chlorine. In one embodiment $R^5$ and $R^6$ are hydrogen.

In another embodiment $R^1$ is hydrogen and $R^2$, $R^3$, $R^4$, $R^5$, and $R^6$ are as defined above in Formulas II-V. In a further embodiment $R^1$ is hydrogen, $R^2$ is methyl, $R^3$, $R^4$, $R^5$ and $R^6$ are as defined above in Formulas II-V.

In a further embodiment, $R^1$ is hydrogen, $R^2$ is methyl, $R^4$ is hydrogen, and $R^3$, $R^5$ and $R^6$ are as defined above in Formulas II-V.

In a further embodiment, $R^1$ is hydrogen, $R^2$ is methyl, $R^4$ is hydrogen, $R^3$ is hydrogen, halogen or methoxy, and the halogen is selected from the group consisting of fluoro or chloro, and $R^5$ and $R^6$ are as defined above in Formulas II-V.

In a further embodiment, $R^1$ is hydrogen, $R^2$ is methyl, $R^4$ is hydrogen, $R^3$ is hydrogen, halogen or methoxy, and the halogen is selected from the group consisting of fluoro or chloro, and $R^5$ and $R^6$ are hydrogen.

In a further embodiment, the present invention relates to compounds of the Formula VI-X

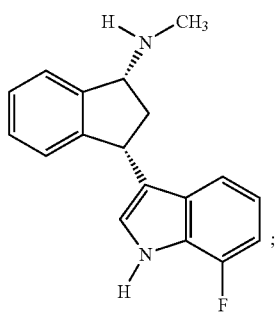

(VI)

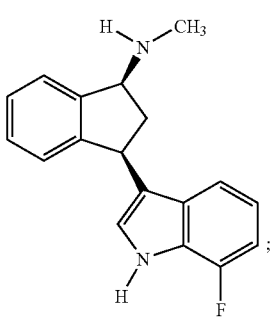

(VII)

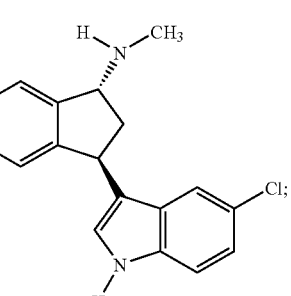

(VIII)

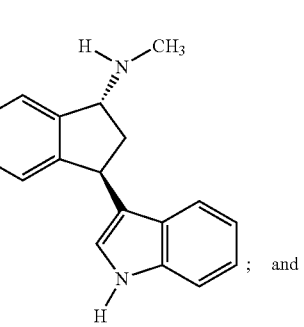

(IX)

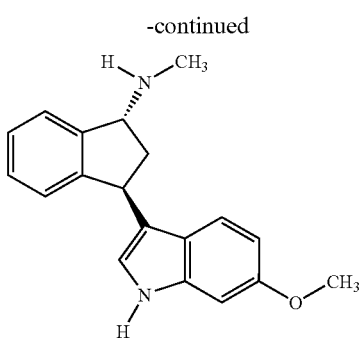

(X)

or a pharmaceutically acceptable salt thereof.

As used herein, it is understood that compounds of Formula I-X are meant to include all the examples exemplified herein.

In the present invention the term Halogen means fluoro, chloro, bromo or iodo.

In the present invention, the term "$C_1$-$C_8$ straight or branched alkyl" refers to a saturated hydrocarbon having from one to eight carbon atoms inclusive. Examples of such substituents include, but are not limited to, methyl, ethyl, 1-propyl, 2-propyl, 1-butyl, 2-butyl, 2-methyl-2-propyl, 2-methyl-1-propyl, n-pentyl and n-octyl.

Furthermore, the term "$C_3$-$C_8$ cycloalkyl" refers to a saturated cyclohydrocarbon ring having from three to eight carbon atoms inclusive. Included within this term are cyclopropyl, cyclobutyl, cyclopentyl, cyclohexyl, cyclohexyl and cyclooctyl.

The term "$C_1$-$C_5$-alkoxy" refers to a saturated alkoxy group having from one to five carbon atoms inclusive with the open valency on the oxygen. Examples of such substituents include, but are not limited to, methoxy, ethoxy, n-butoxy, t-butoxy and n-pentyloxy.

The term "$C_1$-$C_8$ straight or branched polyfluoroalkyl" refers to a saturated hydrocarbon having from one to eight carbon atoms inclusive substituted with one or more fluorine atoms. Examples of such substituents include, but are not limited to, trifluoromethyl, pentafluoroethyl, 1-fluoroethyl and 1,2-difluoroethyl and 2,3-difluorooctyl.

A "therapeutically effective amount" of a compound as used herein means an amount sufficient to cure, alleviate or partially arrest the clinical manifestations of a given disease and/or its complications. An amount adequate to accomplish this is defined herein as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatment are two separate aspect of the invention. The patient to be treated, i.e. the patient in need thereof, may be a mammal, in particular a human being.

The salts of the invention are may be acid addition salts. The acid addition salts of the invention are may be pharmaceutically acceptable salts of the compounds of the invention formed with non-toxic acids. Acid addition salts include salts of inorganic acids as well as organic acids. Examples of suitable inorganic acids include hydrochloric, hydrobromic, hydroiodic, phosphoric, sulfuric, sulfamic, nitric acids and the like. Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in *J. Pharm. Sci.* 1977, 66, 2, which is incorporated herein by reference.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric centres and it is intended that any isomers (i.e. enantiomers or diastereomers), as separated, pure or partially purified and any mixtures thereof including racemic and diastereomeric mixtures, i.e. a mixture of stereoisomers, are included within the scope of the invention.

Racemic forms can be resolved into the optical antipodes by known methods, for example, by fractional separation of diastereomeric salts thereof with an optically active acid, and liberating the optically active amine compound by treatment with a base. Another method for resolving racemates into the optical antipodes is based upon chromatography on an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials, by stereoselective synthesis or by enzymatic resolution.

The pharmaceutical compositions of this invention, or those which are manufactured in accordance with this invention, may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients or other additives normally used in the art may be used. Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, such as sterile water, adjusting the solution to desired volume, sterilizing the solution and filling it in suitable ampules or vials. Any suitable additive conventionally used in the art may be added, such as tonicity agents, preservatives, antioxidants, etc.

Conveniently, the compounds of the invention may be formulated in a unit dosage form, each dosage containing from about 0.01 to about 1000 mg, or from about 0.05 to about 5000, or from about 0.1 to about 1000 mg, the actual dosage may however vary e.g. according to the specific compound. The term "unit dosage form" refers to physically discrete units suitable as unitary dosages for human subjects and other mammals, each unit containing a predetermined quantity of active material calculated to produce the desired therapeutic effect, in association with one or more pharmaceutically acceptable carriers, diluents, excipients or other additives normally used in the art.

The compounds of the invention are effective over a wide dosage range. For example, dosages per day normally fall within the range of about 0.01 to about 100 mg/kg of body weight, or within the range of about 0.1 to about 75 mg/kg. However, it will be understood that the amount of the compound actually administered will be determined by a physician, according to the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

All references cited throughout the specification are hereby incorporated by reference in their entirety.

General Methods of Preparation of Intermediates for the Synthesis of Compounds of the Invention 7-Fluoroindole was synthesized according to: Bartoli, Guiseppe; Palmieri, Gianni; Bosco, Marcella; Dalpozzo, Renato; Tetrahedron Lett., 30, 16, 1989, 2129-2132.

Indole, 5-Chloroindole and 6-methoxyindole were purchased from Aldrich.

Method 1: 3-(1H-Indol-3-yl)-indan-1-ones 3-(1H-Indol-3-yl)-indan-1-ones can be prepared as shown in Scheme 1.

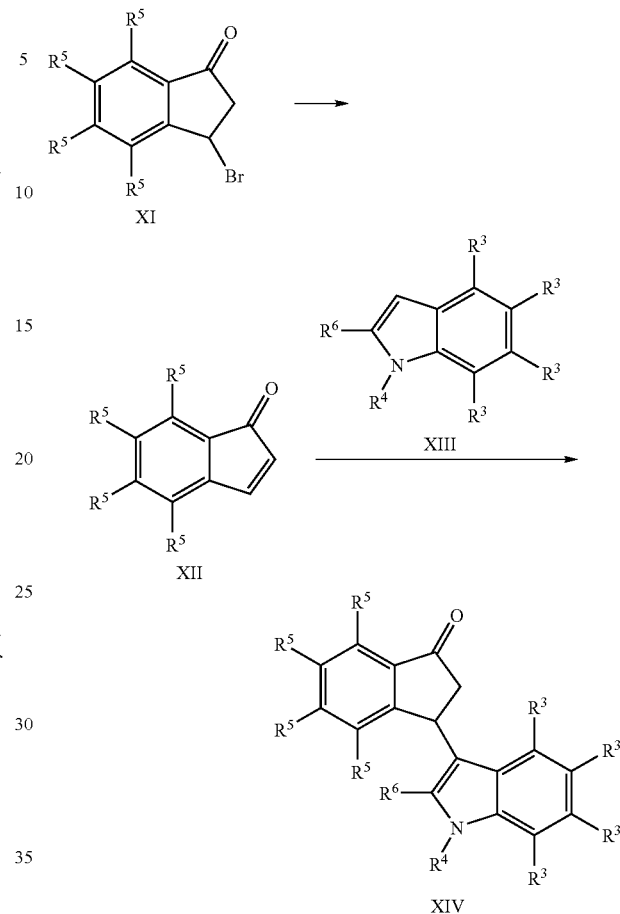

$R^3$, $R^4$, $R^5$ and $R^6$ are as defined above.

3-Bromo-indan-1-ones of general Formula XI are treated with a base such as triethylamine to form inden-1-ones of general Formula XII. Treatment of inden-1-ones of general Formula XII with indoles of general Formula XIII in the presence of a Lewis acid catalyst such as scandium triflate or copper triflate give 3-(1H-indol-3-yl)-indan-1-ones of general Formula XIV.

Method 2: cis-3-(1H-Indol-3-yl)-indan-1-ols cis-3-(1H-Indol-3-yl)-indan-1-ols of general Formula XV are prepared as shown in Scheme 2.

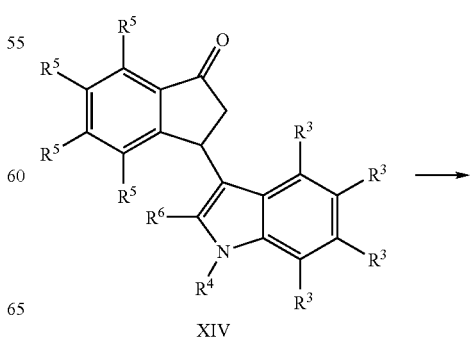

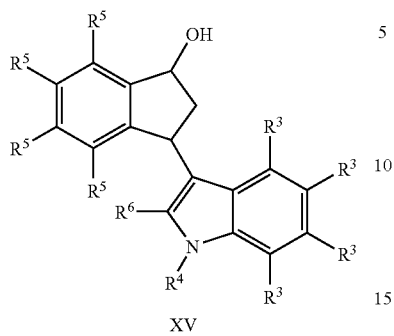

XV $R^3$-$R^6$ are as defined above.

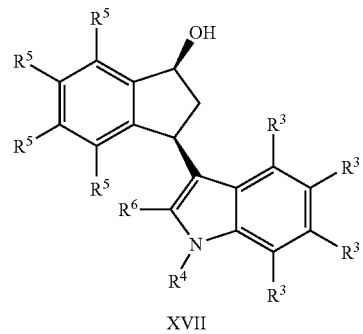

XVII $R^3$-$R^6$ are as defined above, and $R^7$ is a $C_1$—$C_8$ straight or branched alkyl group.

3-(1H-Indol-3-yl)-indan-1-ones of general Formula XIV are treated with a reducing agent such as sodium borohydride to give cis-3-(1H-indol-3-yl)-indan-1-ols of general Formula XV.

Method 3: Enzymatic chiral resolution of cis-3-(1H-indol-3-yl)-indan-1-ols cis-3-(1H-Indol-3-yl)-indan-1-ols of general Formula XV are resolved into their enantiomers as shown in Scheme 3.

Scheme 3.

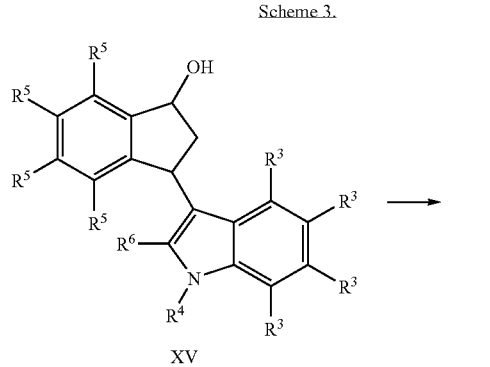

XV

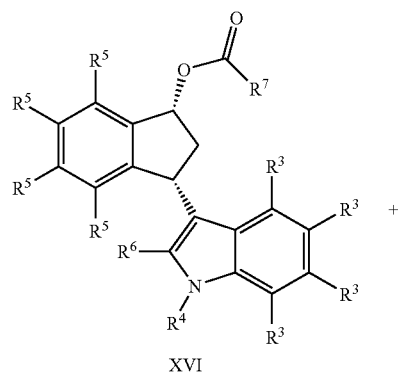

XVI cis-3-(1H-Indol-3-yl)-indan-1-ols of general Formula XV are resolved into their enantiomers by treatment of racemic cis-3-(1H-indol-3-yl)-indan-1-ols with an irreversible acyl donor such as vinyl butyrate in the presence of a lipase such as Novozym 435 (Availabale from Novozymes A/S, Krogshoejvej 36, 2880 Bagsvaerd, Denmark). One enantiomer is then esterificated to form ester of general Formula XVI while the other enantiomer of general Formula XVII is left unreacted. The compounds of general Formulae XVI and XVII are separated by standard chromatographic techniques.

Method 4: Optically active cis-3-(1H-indol-3-yl)-indan-1-ols

Optically active cis-3-(1H-indol-3-yl)-indan-1-ols of general Formula XVIII are obtained by hydrolysis of esters of general Formula XVI or by treatment of esters of general formula XVI with a transesterification reagent such as sodium methoxide in methanol as shown in Scheme 4.

Scheme 4.

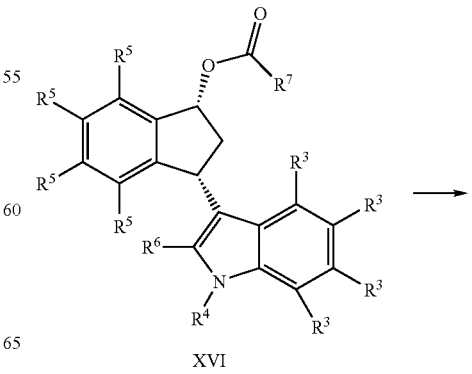

XVI

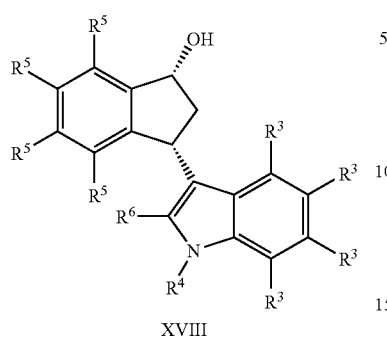

XVIII

R³-R⁶ are as defined above, and R⁷ is a C₁—C₈ straight or branched alkyl group.

Method 5: Optically active
3-(1H-indol-3-yl)-indan-1-ones

Optically active cis-3-(1H-indol-3-yl)-indan-1-ols of general Formulae XVII and XVIII are oxidized by an oxidant such as the Dess-Martin periodane to give optically active 3-(1H-indol-3-yl)-indan-1-ones general Formulae XIX and XX as shown in Scheme 5.

Scheme 5.

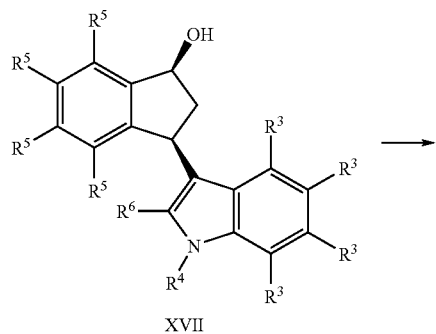

XVII

XIX

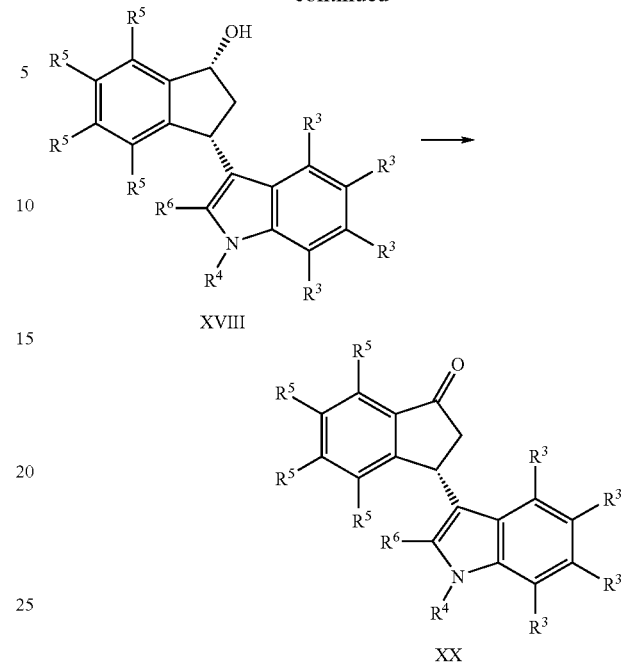

XVIII

XX

R³-R⁶ are as defined above.

Method 6: trans-3-(3-Azido-indan-1-yl)-1H-indoles trans-3-(3-Azido-indan-1-yl)-1H-indoles of general Formula XXI are prepared as shown in Scheme 6.

Scheme 6.

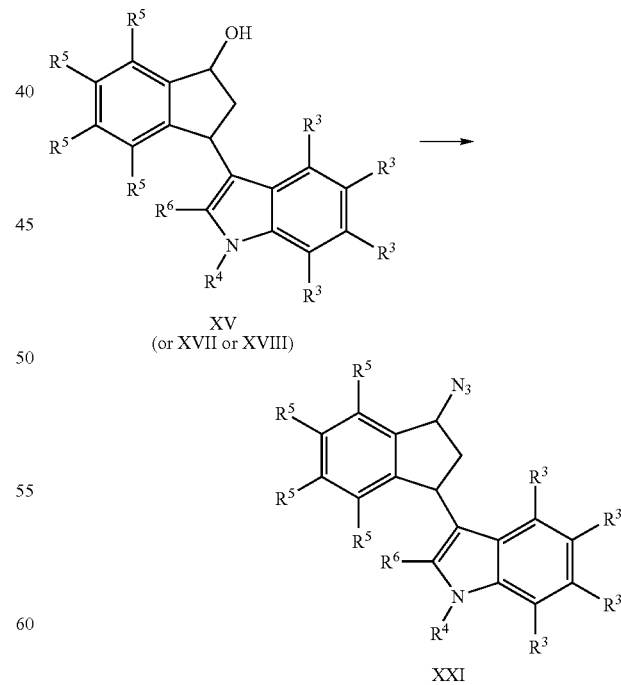

XV
(or XVII or XVIII)

XXI

R³-R⁶ are as defined above.

Treatment of racemic cis-3-(1H-indol-3-yl)-indan-1-ols of general Formulae XV or treatment of optically active cis-3-

(1H-indol-3-yl)-indan-1-ols of general Formulae XVII or XVIII with an azidating reagent such as diphenyl phosphoryl azide and a base such as DBU provides racemic or optically active trans-3-(3-azido-indan-1-yl)-1H-indoles of general Formula XXI, respectively.

Method 7: trans-[3-(3-Azido-indan-1-yl)-indol-1-yl]-phosphonic acid diphenyl esters trans-[3-(3-Azido-indan-1-yl)-indol-1-yl]-phosphonic acid diphenyl esters of general Formula XXII are prepared as shown in Scheme 7.

Scheme 7.

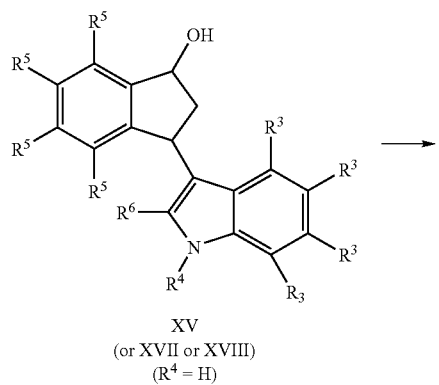

XV
(or XVII or XVIII)
($R^4$ = H)

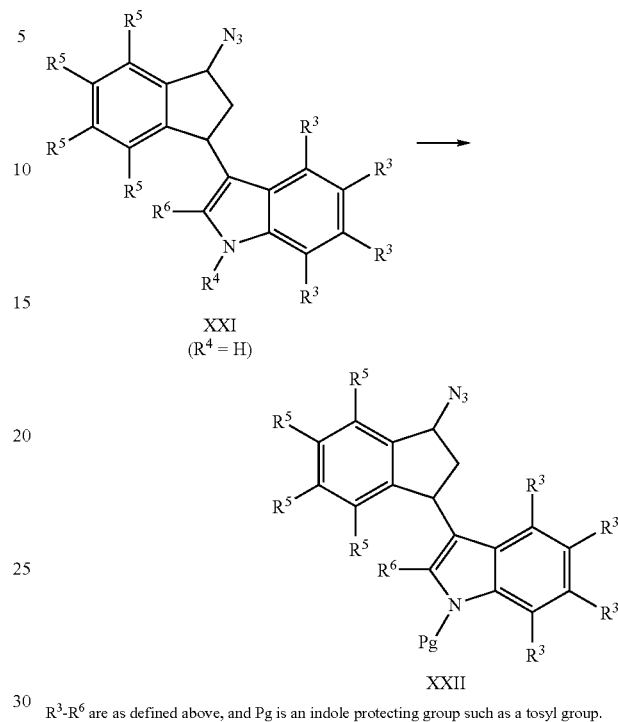

XXII
$R^3$-$R^6$ are as defined above, and Pg is an indole protecting group such as a diphenyl phosphoryl group.

Treatment of racemic cis-3-(1H-indol-3-yl)-indan-1-ols of general Formulae XV with $R^4$=H or treatment of optically active cis-3-(1H-indol-3-yl)-indan-1-ols of general Formulae XVII or XVIII with $R^4$=H with an excess of diphenyl phosphoryl azide and a base such as DBU provides racemic or optically active trans-[3-(3-azido-indan-1-yl)-indol-1-yl]-phosphonic acid diphenyl esters of general formula XXII, respectively.

Method 8: N-protected trans-3-(3-azido-indan-1-yl)-1H-indoles

N-protected trans-3-(3-azido-indan-1-yl)-1H-indoles of general Formula XXII are prepared by the treatment of trans-3-(3-azido-indan-1-yl)-1H-indoles of general Formula XXI with $R^4$=H with an appropriate protection group reagent such as p-tolouensulfonic acid chloride as shown in Scheme 8.

Scheme 8.

XXI
($R^4$ = H)

XXII
$R^3$-$R^6$ are as defined above, and Pg is an indole protecting group such as a tosyl group.

General Methods of Preparation of the Compounds of the Invention

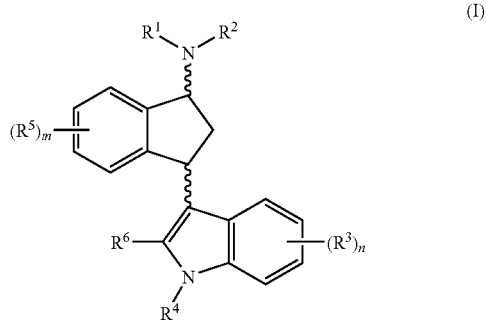

(I)

Method 9: trans-3-(1H-Indol-3-yl)-indan-1-ylamines

Racemic or optically active trans-3-(1H-indol-3-yl)-indan-1-ylamines of general Formula XXIII are prepared by the reduction of racemic or optically active trans-3-(3-azido-indan-1-yl)-1H-indoles of general Formula XXI or racemic or optically active N-protected trans-3-(3-azido-indan-1-yl)-1H-indoles of general Formula XXII under appropriate reducing conditions such as addition of sodium borohydride, in the presence of an appropriate transition metal catalyst such as Pd/C under hydrogen or treatment with a trimethyl phosphine in pyridine and aqueous ammonium hydroxide as shown in Scheme 9, respectively.

Scheme 9.

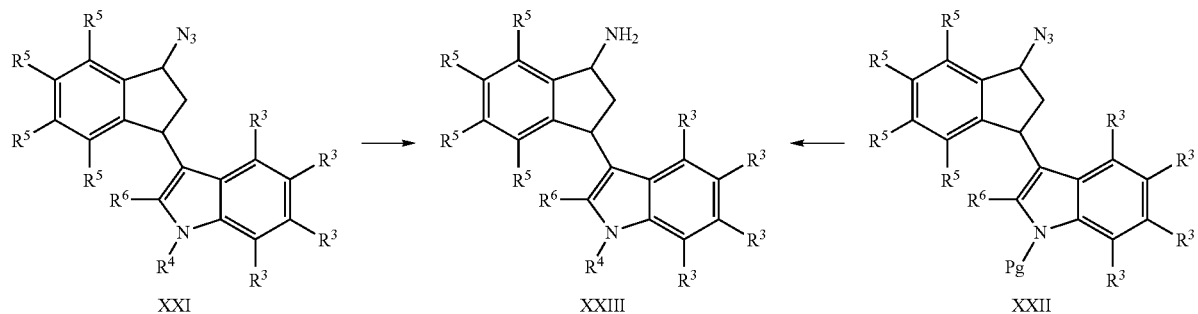

$R^3$-$R^6$ are as defined above, and Pg is an indole protecting group such as a diphenyl phosphoryl group.

Method 10: cis-3-(1H-Indol-3-yl)-indan-1-ylamines

Racemic or optically active cis-3-(1H-indol-3-yl)-indan-1-ylamines of general Formula XXV with $R^1$=H are prepared as shown in Scheme 10.

Scheme 10.

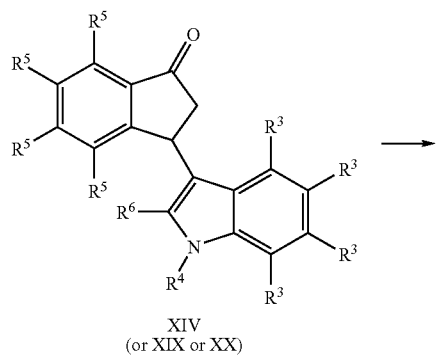

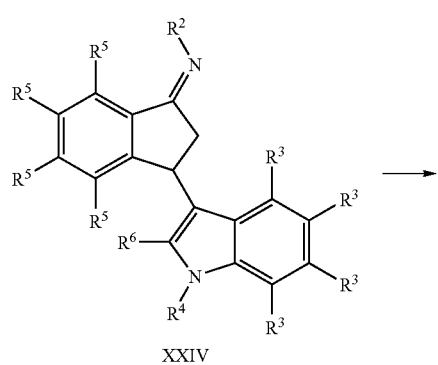

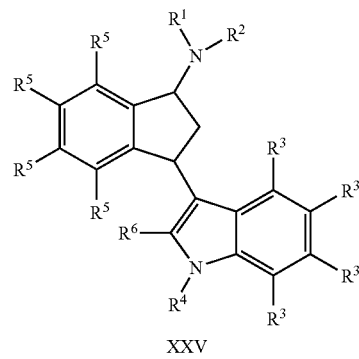

$R^1$ = H and $R^2$, $R^3$-$R^6$ are as defined above.

Racemic or optically active 3-(1H-indol-3-yl)-indan-1-ones of general Formula XIV, XIX or XX are treated with an amine (NH$_2$R$^2$) and a drying reagent such as tetraethoxy silane to give imines of Formula XXIV, which are reduced using a reducing agent such as sodium borohydride or by treatment with hydrogen in the presence of transition metal catalyst such as PtO$_2$ to give racemic or optically active cis-3-(1H-Indol-3-yl)-indan-1-ylamines of general Formula XXV with $R^1$=H.

Method 11: cis-3-(1H-Indol-3-yl)-indan-1-ylamines

Racemic or optically active cis-3-(1H-indol-3-yl)-indan-1-ylamines of general Formula XXV are prepared as shown in Scheme 11.

Scheme 11.

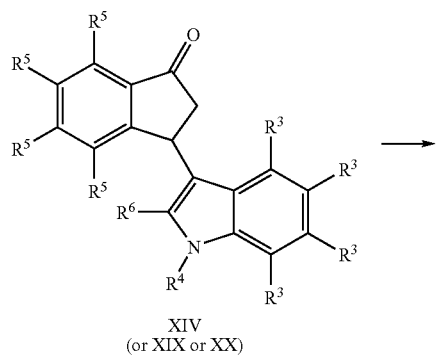

XIV
(or XIX or XX)

$R^1$-$R^6$ are as defined above.

A 3-(1H-Indol-3-yl)-indan-1-one of general Formula XIV, XIX or XX are treated with an amine (NHR$^1$R$^2$) and a reducing reagent such as sodium cyanoborohydride in an acetic acid/methanol solution of appropriate pH to give racemic or optically active cis-3-(1H-indol-3-yl)-indan-1-ylamines of general Formula XXV, respectively.

Method 12: cis-3-(1H-Indol-3-yl)-indan-1-ylamines and trans-3-(1H-Indol-3-yl)-indan-1-ylamines

Scheme 12.

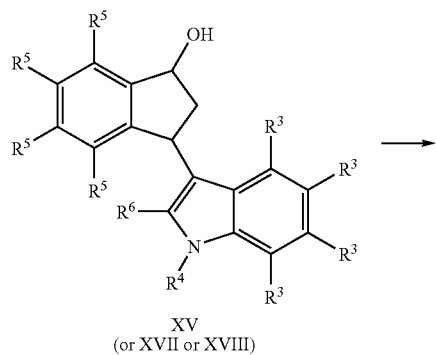

XV
(or XVII or XVIII)

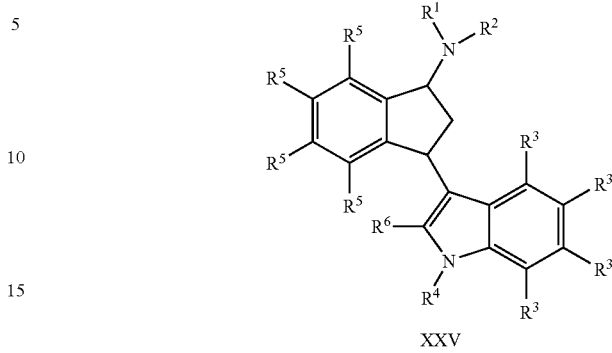

XXV $R^1$-$R^6$ are as defined above.

Treatment of racemic cis-3-(1H-indol-3-yl)-indan-1-ols of general Formulae XV or treatment of optically active cis-3-(1H-indol-3-yl)-indan-1-ols of general Formulae XVII or XVIII with an alcohol-activating reagent and a base such as triethyl amine followed reaction with an amine (NHR$^1$R$^2$) provides a mixture of racemic or optically active cis- and trans-3-(1H-indol-3-yl)-indan-1-ylamines of general Formula XXV, which are separated by standard chromatographic methods such as HPLC or flash chromatography to give racemic or optically active cis-3-(1H-indol-3-yl)-indan-1-ylamines of general Formula XXV or racemic or optically active trans-3-(1H-indol-3-yl)-indan-1-ylamines of general Formula XXV as shown in Scheme 12.

Method 13: trans-3-(1H-Indol-3-yl)-indan-1-ylamines trans-3-(1H-Indol-3-yl)-indan-1-ylamines of general Formula XXVI with R$^1$, R$^4$=H are prepared by the treatment of N-protected trans-3-(3-azido-indan-1-yl)-1H-indoles of general Formula XXII with (R$^1$)$_2$BBr followed by removal of the indole protection group as shown in Scheme 13.

Scheme 13.

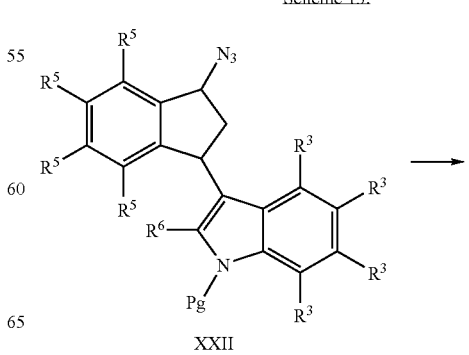

XXII

-continued

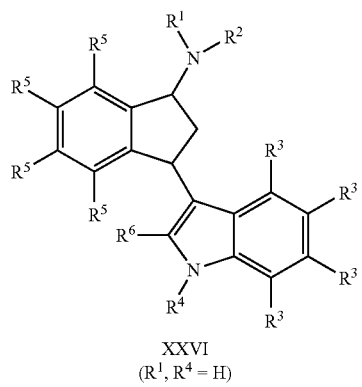

XXVI
(R¹, R⁴ = H)

R², R³, R⁵ and R⁶ are as defined above, and Pg is an indole protection group such as a tosyl group or a diphenyl phosphoryl group.

Method 14:
trans-3-(1H-Indol-3-yl)-indan-1-ylamines trans-3-(1H-Indol-3-yl)-indan-1-ylamines of general Formula XXVI with $R^1$, $R^4$=H are prepared by the treatment of trans-3-(1H-Indol-3-yl)-indan-1-ylamines of general Formula XXIII with $R^4$=H with methyl chloroformate followed by reduction with an appropriate reducing reagent such as lithium aluminum hydride as shown in Scheme 14.

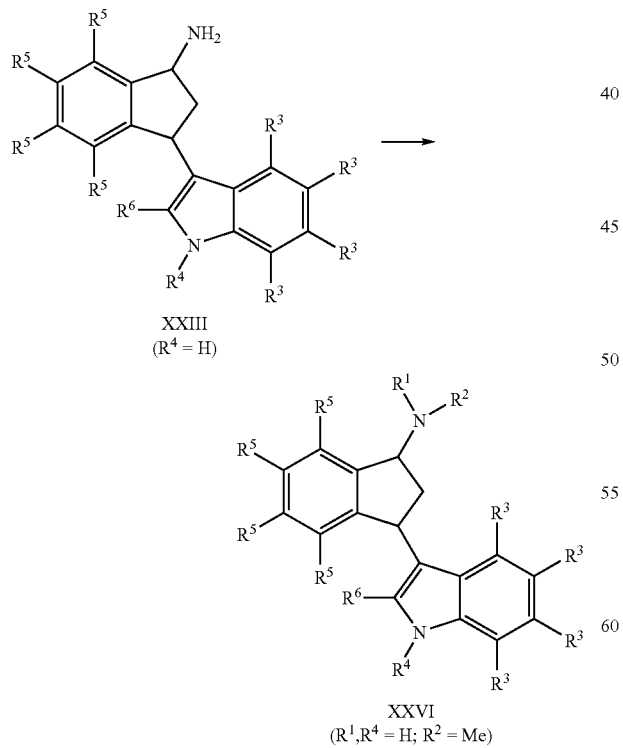

R³, R⁵ and R⁶ are as defined above.

Method 15: Optically active
3-(1H-Indol-3-yl)-indan-1-ylamines

Racemic cis- or trans-3-(1H-indol-3-yl)-indan-1-ylamines of general Formula XXV and XXVI are separated into their pairs of optically active cis- or trans-3-(1H-indol-3-yl)-indan-1-ylamines, respectively, by chromatographic techniques such as chiral supercritical fluid chromatography (SFC) and chiral HPLC.

Method 16: Optically active
3-(1H-Indoly-3-yl)indan-1-ylamines

Racemic cis- or trans-3-(1H-indol-3-yl)-indan-1-ylamines of general Formula XXV and XXVI are separated into their pairs of optically active cis- or trans-3-(1H-indol-3-yl)-indan-1-ylamines, respectively, by fractional separation of diastomeric salts with an optically active acid and liberated the optically active amine compound by treatment with a base.

Experimental Section

LC-MS Methods A and B, general: Solvent system: A=water/TFA (100:0.05) and B=water/acetonitrile/TFA (5:95:0.035) (TFA=trifluoroacetic acid). Purity was determined by integration of the UV (254 nm) and ELSD trace and retention times (RT) are expressed in minutes. MS instruments are from PESciex (API), equipped with APPI-source and operated in positive ion mode.

Method A: API 150EX and Shimadzu LC8/SLC-10A LC system. Column: 30×4.6 mm Waters Symmetry C18 with 3.5 µM particles operated at room temperature. Linear Gradient elution with 90% A to 100% B in 4 min and a flow rate of 2 ml/min.

Method B: API 150EX and Shimadzu LC8/SLC-10A LC system. Column: 30×4.6 mm Waters Symmetry C18 with 3.5 µM particles operated at 40° C. Linear Gradient elution with 90% A to 100% B in 2.4 min and a flow rate of 3.3 ml/min.

LC-MS TOF (TOF=time of flight) Method C: micromass LCT 4-ways MUX equipped with a Waters 2488/Sedex 754 detector system. Column: 30×4.6 mm Waters Symmetry C18 column with 3.5 µm particle size operated at room temperature. Linear Gradient elution with 90% A to 100% B in 4 min and a flow rate of 2 ml/min. Purity was determined by integration of the UV (254 nm) and ELSD trace and retention times (RT) are expressed in minutes.

$^1$H NMR and $^{13}$C NMR spectra were recorded on a Bruker DRX 500 at 500.13 MHz and 125.67, respectively. Deuterated chloroform (99.8% D) or dimethylsulfoxide (99.9% D) were used as solvents. TMS was used as internal reference standard. Chemical shifts are expressed as ppm values. The following abbreviations are used for multiplicity of NMR signals: s=singlet, d=doublet, t=triplet, q=quartet, qv=quintet, h=heptet, dd=double doublet, dt=double triplet, dq=double quartet, tt=triplet of triplets, m=multiplet, b=broad.

EXAMPLES

Synthesis of 3-bromo-indan-1-one 390 g (2.2 mol) N-bromosuccinimde (powder with no lumps) and 0.5 g benzoyl peroxide were added to 264 g indan-1-one in 1500 mL CCl₄ and refluxed with mechanical stirring for 1.5 hours. The colour of the reaction mixture suddenly changed to yellow and all N-bromosuccinimde (heavier than CCl₄) was converted to succinimide (lighter than CCl4). The reaction mixture was cooled to 20° C., filtered and concentrated in vacuo. Crude 3-bromo-indan-1-one was dissolved in 600 mL ethyl acetate/heptane (1:2), cooled 2 hours on an ice bath and then left in a freezer over night to give 257 g crystals of 3-bromo-indan-1-one (62% yield).

Synthesis of 3-(7-fluoro-1H-indol-3-yl)-indan-1-one (Method 1)

Triethylamine (4.5 mL; 32 mmol; 1.2 equiv.) was added to 3-bromo-indan-1-one (5.6 g; 27 mmol) in 100 mL THF at 0° C. and stirred 1 h at r.t. The reaction mixture was filtered to remove triethylammonium bromide and concentrated in vacuo to give inden-1-one. 7-Fluoroindole (3.3 g, 22 mmol) and Sc(OTf)$_3$ (550mg, 5 mol %) were added to inden-1-one in 100 mL CH$_2$Cl$_2$ at 0° C. The reaction mixture was allowed to warm to room temperature over night. 100 mL ethyl acetate was added and the mixture was filtered through a silica gel plug and concentrated in vacuo. After flash chromatography (heptane/ethyl acetate, silica gel) 5.9 g 3-(7-fluoro-1H-indol-3-yl)-indan-1-one (82%) was isolated.

The following compounds were synthesized in a similar way:
3-(1H-indol-3-yl)-indan-1-one
3-(1-Methyl-1H-indol-3-yl)-indan-1-one
3-(5-Fluoro-1H-indol-3-yl)-indan-1-one
3-(6-Fluoro-1H-indol-3-yl)-indan-1-one
3-(6-Methoxy-1H-indol-3-yl)-indan-1-one
3-(5-Fluoro-2-methyl-1H-indol-3-yl)-indan-1-one
3-(4-Chloro-1H-indol-3-yl)-indan-1-one
3-(5-Chloro-1H-indol-3-yl)-indan-1-one
3-(7-Chloro-1H-indol-3-yl)-indan-1-one
5-Fluoro-3-(7-methyl-1H-indol-3-yl)-indan-1-one
3-(6-Bromo-1H-indol-3-yl)-5-fluoro-indan-1-one
3-(4-Chloro-1H-indol-3-yl)-6-fluoro-indan-1-one
3-(4,6-Difluoro-1H-indol-3-yl)-6-fluoro-indan-1-one
3-(4-Chloro-1H-indol-3-yl)-6-methoxy-indan-1-one
3-(5,6-Difluoro-1H-indol-3-yl)-6-methoxy-indan-1-one
5-Chloro-3-(5-fluoro-1H-indol-3-yl)-indan-1-one
3-(6-Chloro-3-oxo-indan-1-yl)-1H-indole-5-carbonitrile
6-Chloro-3-(5-methoxy-1H-indol-3-yl)-indan-1-one
6-Chloro-3-(7-methoxy-1H-indol-3-yl)-indan-1-one Synthesis of cis-3-(1H-indol-3-yl)-indan-1-ol (Method 2)

NaBH$_4$ (6.2 g, 163 mmol, 2 equiv.) was added to 3-(1H-indol-3-yl)-indan-1-one (20 g, 80.9 mmol) in 200 mL methanol and 100 mL THF at 0° C. The reaction mixture was allowed to warm to room temperature over night. Aqueous work up gave racemic cis-3-indolyl-indan-1-ol (quantitative).

The following compounds were synthesized in a similar way:
cis-3-(6-Fluoro-1H-indol-3-yl)-indan-1-ol
cis-3-(6-Methoxy-1H-indol-3-yl)-indan-1-ol
cis-3-(5-Chloro-1H-indol-3-yl)-indan-1-ol
cis-3-(4-Chloro-1H-indol-3-yl)-6-fluoro-indan-1-ol
cis-6-Chloro-3-(5-methoxy-1H-indol-3-yl)-indan-1-ol Synthesis of butyric acid (1R,3S)-3-(1H-indol-3-yl)-indan-1-yl ester and (1S,3R)-3-(1H-indol-3-yl)-indan-1-ol (Method 3)

Novozym 435 (1g) (Available from Novozymes A/S, Krogshoejvej 36, 2880 Bagsvaerd, Denmark) and vinyl butyrate (20.5 mL, 162 mmol) were added to racemic cis-3-indolyl-indan-1-ol (80.9 mmol) in 200 mL toluene. The reaction mixture was shaken for 2 days under argon until $^1$H-NMR shows 50% conversion. The reaction mixture was filtered and concentrated in vacuo. After flash chromatography (heptane/ethyl acetate, silica gel) 13.49 g butyric acid (1R,3S)-3-(1H-indol-3-yl)-indan-1-yl ester and 9.78 g (1S,3R)-3-(1H-indol-3-yl)-indan-1-ol were isolated.

The following compounds were synthesized in a similar way:
Butyric acid (1R,3S)-3-(7-fluoro-1H-indol-3-yl)-indan-1-yl ester
(1S,3R)-3-(7-Fluoro-1H-indol-3-yl)-indan-1-ol
(1S,3R)-3-(5-Chloro-1H-indol-3-yl)-indan-1-ol
(1S,3R)-3-(6-Methoxy-1H-indol-3-yl)-indan-1-ol Synthesis of (1R,3S)-3-(1H-indol-3-yl)-indan-1-ol (Method 4)

3 mL 30% NaOMe in methanol was added to 13.49 g butyric acid (1R,3S)-3-(1H-indol-3-yl)-indan-1-yl ester in 100 mL methanol. TLC showed full conversion after 1.5 hours. 1.5 g solid NH$_4$Cl and 50 mL water were added. Methanol was removed in vacuo and after aqueous work up, (1R,3S)-3-(1H-indol-3-yl)-indan-1-ol (37.9 mmol) was obtained.

The following compound was synthesized in a similar way:
(1R,3S)-3-(7-Fluoro-1H-indol-3-yl)-indan-1-ol Synthesis of (R)-3-(1H-indol-3-yl)-indan-1-one (Method 5)

Dess-Martin Periodane (1.08 g, 2.55 mmol) in 10 mL CH$_2$Cl$_2$ was added to (1S,3R)-3-(1H-Indol-3-yl)-indan-1-ol (2.52 mmol) in 10 mL CH$_2$Cl$_2$ at 0° C. The reaction mixture was allowed to warm to room temperature and stirred 40 min—TLC showed full conversion. To the reaction mixture ethyl acetate and sat. NaHCO$_3$ was added. The organic phase was isolated, washed with 2N NaOH and brine, dried over MgSO$_4$ and concentrated in vacuo. A quantitative yield of (R)-3-(1H-indol-3-yl)-indan-1-one was obtained after flash chromatography (heptane/ethyl acetate, silica gel).

The following compounds were synthesized in a similar way:
(R)-3-(7-Fluoro-1H-indol-3-yl)-indan-1-one
(S)-3-(7-Fluoro-1H-indol-3-yl)-indan-1-one Synthesis of 3-((1S,3S)-3-azido-indan-1-yl)-1H-indole (Method 6)

1,8-Diazabicyclo[5.4.0]undec-7-ene (4.8 mL, 32.1 mmol, 1.45 equiv) was added to (1R,3S)-3-(1H-indol-3-yl)-indan-1-ol (22.2 mmol) and diphenyl phosphoryl azide (6.0 mL, 27.8 mmol, 1.25 equiv) in 150 mL dry THF at 0° C. The reaction was stirred 0.5 hours at 0° C., then 2 hours at room temperature—TLC showed full conversion. The reaction mixture was poured into water and extracted with ethyl acetate. The organic phase was washed with 100 mL 0.5 N HCl, sat. NaHCO$_3$, dried over MgSO$_4$ and concentrated in vacuo to give the 3-((1S,3S)-3-azido-indan-1-yl)-1H-indole.

The following compound was synthesized in a similar way:
3-((1R,3R)-3-Azido-indan-1-yl)-6-methoxy-1H-indole Synthesis of [3-((1R,3R)-3-azido-indan-1-yl)-5-chloro-indol-1-yl]-phosphonic acid diphenyl ester (Method 7)

Diphenyl phosphoryl azide (23 g, 85 mmol) was added to (1S,3R)-3-(5-chloro-1H-indol-3-yl)-indan-1-ol (10 g, 35 mmol) in 150 mL dry THF at 5° C. 1,8-diazabicyclo[5.4.0]undec-7-ene (13.7 mL, 92 mmol) was added over 0.5 hours. The reaction mixture was stirred over night while warming to room temperature. The reaction mixture was poured into brine and extracted with Et$_2$O. The organic phase was washed with 100 mL 0.1 N HCl, 0.1 N NaOH, dried over MgSO$_4$ and concentrated in vacuo. After flash chromatography. (heptane/ethyl acetate, silica gel), 19.1 g [3-((1R,3R)-3-azido-indan-1-yl)-5-chloro-indol-1-yl]-phosphonic acid diphenyl ester was isolated.

The following racemic compounds were synthesized in a similar way:
[3-(3-Azido-indan-1-yl)-indol-1-yl]-phosphonic acid diphenyl ester
[3-(3-Azido-indan-1-yl)-6-fluoro-indol-1-yl]-phosphonic acid diphenyl ester
[3-(3-Azido-indan-1-yl)-6-methoxy-indol-1-yl]-phosphonic acid diphenyl ester
[3-(3-Azido-5-fluoro-indan-1-yl)-4-chloro-indol-1-yl]-phosphonic acid diphenyl ester
[3-(3-Azido-5-chloro-indan-1-yl)-5-methoxy-indol-1-yl]-phosphonic acid diphenyl ester Synthesis of 3-((1R,3R)-3-azido-indan-1-yl)-6-methoxy-1-(toluene-4-sulfonyl)-1H-indole (Method 8)

1 g Sodium hydride (60% in mineral oil) was added to 2 g 3-((1R,3R)-3-azido-indan-1-yl)-6-methoxy-1H-indole in 50 mL dry THF at 5° C. and the reaction mixture was stirred 1 hour at 5° C. 2 g p-toluene sulfonic acid chloride was added in portions at 5° C. and stirring was continued for another 4 hours. Ice was added and after 1 hour water and ethyl acetate was added. The organic phase was separated and washed with brine, dried over MgSO$_4$ and concentrated in vacuo. After flash chromatography (heptane/ethyl acetate, silica gel), 2.5 g 3-((1R,3R)-3-azido-indan-1-yl)-6-methoxy-1-(toluene-4-sulfonyl)-1H-indole was isolated.

The following compound was synthesized in a similar way:
3-((1R,3R)-3-Azido-indan-1-yl)-1-(toluene-4-sulfonyl)-1H-indole Synthesis of (1R,3R)-3-(5-chloro-1H-indol-3-yl)-indan-1-ylamine (Method 9)

32 g Trimethyl phosphine was added over 2 hours to 19 g [3-((1R,3R)-3-azido-indan-1-yl)-5-chloro-indol-1-yl]-phosphonic acid diphenyl ester in 100 mL pyridine and 36 mL 9N ammonium hydroxide at room temperature. The reaction mixture was stirred over night at room temperature and concentrated in vacuo. Ethyl acetate and water were added. The mixture was made basic with aqueous NaOH and filtered. The organic phase was concentrated in vacuo and was dissolved in ethyl acetate again. The ethyl acetate solution was extracted with 2×250 mL 2N methanesulfonic acid. The aqueous phase was made basic with 9N NaOH to form a precipitate, which was subjected to flash chromatography (ethyl acetate, methanol, triethylamine, silica gel) to give 0.6 g (1R,3R)-3-(5-chloro-1H-indol-3-yl)-indan-1-ylamine. The ethyl acetate phase from above was concentrated in vacuo and was dissolved in 100 mL methanol and 10 mL 30% NaOMe in methanol was added. The reaction mixture was stirred 2 hours at room temperature, concentrated in vacuo and purified by flash chromatography (ethyl acetate, methanol, triethylamine, silica gel) to give further 0.45 g (1R,3R)-3-(5-chloro-1H-indol-3-yl)-indan-1-ylamine.

Synthesis of Example 7: [(1S,3R)-3-(1H-indol-3-yl)-indan-1-yl]-methyl-amine (Method 10)

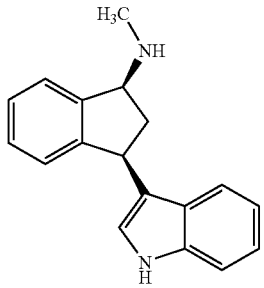

(R)-3-(1H-indol-3-yl)-indan-1-one, methyl amine (5 mL 2M in THF) and 1 mL tetraethoxy silane in 10 mL methanol were stirred 11 minutes at 150° C. under microwave irradiation using the Emry Optimizer™ instrument. PtO$_2$ (10 mg) was added and the reaction mixture was stirred under 1 atm. hydrogen over night at room temperature, filtered and concentrated in vacuo. [(1S,3R)-3-(1H-Indol-3-yl)-indan-1-yl]-methyl-amine was isolated in 66% yield after flash chromatography (ethyl acetate, methanol, triethylamine, silica gel).

The following compounds were synthesized in a similar way:

Example 1

Racemic cis-[3-(5-Fluoro-2-methyl-1H-indol-3-yl)-indan-1-yl]-methyl-amine

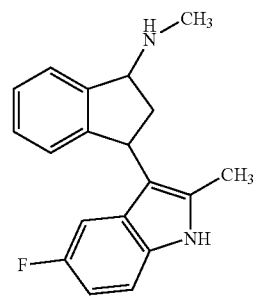

Example 2

Racemic cis-[3-(7-Methoxy-1H-indol-3-yl)-indan-1-yl]-methyl-amine

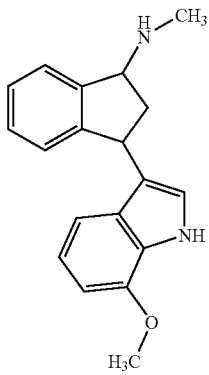

Example 3

Racemic cis-Methyl-[3-(1-methyl-1H-indol-3-yl)-indan-1-yl]-amine

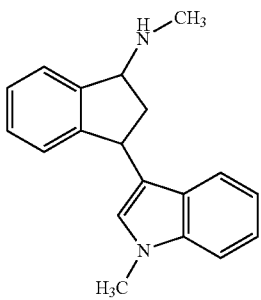

Example 4

Racemic cis-[3-(5-Fluoro-1H-indol-3-yl)-indan-1-yl]-methyl-amine

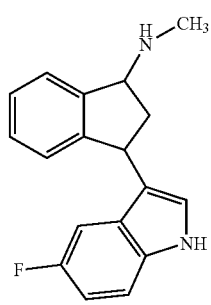

Example 5

Racemic cis-[3-(7-Chloro-1H-indol-3-yl)-indan-1-yl]-methyl-amine

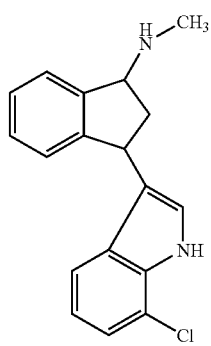

Example 6

Racemic cis-[3-(4-Chloro-1H-indol-3-yl)-indan-1-yl]-methyl-amine

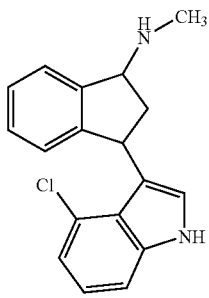

Example 8

[(1R,3S)-3-(7-Fluoro-1H-indol-3-yl)-indan-1-yl]-methyl-amine (Formula VII)

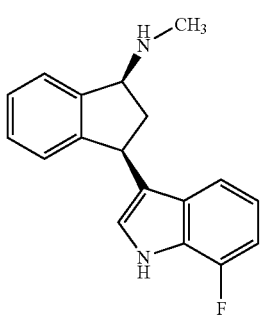

Preparative scale chiral SFC purification (Method 15): Method: Column: Chiralcel OJ-H (2×25 cm) operated at room temperature. Chromatography was carried out using 35% of methanol with 0.1% (v/v) diethylamine as modifier in CO2 (100 bar) and a flow rate 50 ml/min.

Analytical Chiral SFC: Method: Column: 250×4.6 mm Chiralcel AD-H with 5 µM particles operated at room temperature. Chromatography was carried out using 40% of ethanol with 0.1% (v/v) diethylamine as modifier in CO2 (100 bar) and a flow rate 3 ml/min. Detection at 220 nm. $RT_{major}$=2.52 min, $RT_{minor}$=3.29 min, >99.5% ee.

LC/MS: Method A: RT=1.85 min. UV-purity=99.30%, ELSD purity=96.78%

$^1$H-NMR (hydrobromide salt; $d_6$-DMSO): δ 2.23-2.27 (m, 1H), 2.71 (s, 3H), 2.93-2.95 (m, 1H), 4.62 (dd, J=7.8 Hz, 10.2 Hz, 1H), 4.88 (t, J=8.3 Hz, 1H), 6.87-6.96 (m, 3H), 7.12 (d, J=7.7 Hz, 1H), 7.30 (t, J=14.8 Hz, 1H), 7.35-7.38 (m, 2H), 7.72 (d, J=7.6 Hz, 1H), 11.5 (bs, 1H).

Example 9

[(1S,3R)-3-(7-Fluoro-1H-indol-3-yl)-indan-1-yl]-methyl-amine

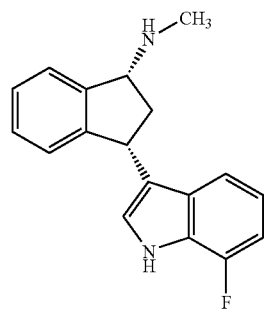

(Formula VI)

Preparative scale chiral SFC purification (Method 15): Method: Column: Chiralcel OJ-H (2×25 cm) operated at room temperature. Chromatography was carried out using 35% of methanol with 0.1% (v/v) diethylamine as modifier in CO2 (100 bar) and a flow rate 50 ml/min.

Analytical Chiral SFC: Method: Column: 250×4.6 mm Chiralcel AD-H with 5 μM particles operated at room temperature. Chromatography was carried out using 40% of ethanol with 0.1% (v/v) diethylamine as modifier in CO2 (100 bar) and a flow rate 3 ml/min. Detection at 220 nm. $RT_{major}$=3.36 min, $RT_{minor}$=2.46 min, >99.5% ee.

LC/MS: Method B: RT=0.90 min. UV-purity=99.80%, ELSD purity=96.08%

$^1$H-NMR (d$_6$-DMSO): δ 1.89-1.96 (m, 1H), 2.15 (bs, 1H), 2.40 (s, 3H), 2.75-2.80 (m, 1H), 4.17 (dd, J=7.3 Hz, 8.7 Hz, 1H), 4.44 (dd, J=7.5 Hz, 10.4 Hz, 1H), 6.82-6.90 (m, 3H), 7.07-7.11 (m, 2H), 7.20 (t, J=7.4 Hz, 1H), 7.26 (d, J=2.2 Hz, 1H), 7.42 (d, J=7.5 Hz, 1H), 11.4 (bs, 1H). $^{13}$C-NMR (d$_6$-DMSO): δ 33.7, 39.4, 63.3, 106.1 ($J_{CF}$=16 Hz), 115.7, 118.5, 118.8, 124.0, 124.1, 124.3, 124.8, 124.9, 126.6, 127.2, 130.8, 145.7, 146.2, 149.7 ($J_{CF}$=243 Hz).

Example 11

Racemic cis-[6-Chloro-3-(7-methoxy-1H-indol-3-yl)-indan-1-yl]-methyl-amine

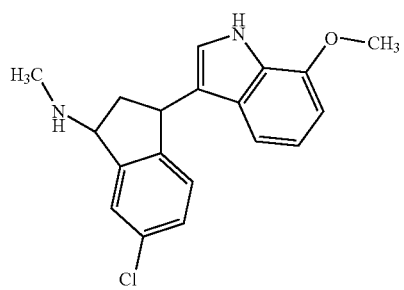

Example 12

Racemic cis-[3-(4-Chloro-1H-indol-3-yl)-6-methoxy-indan-1-yl]-methyl-amine

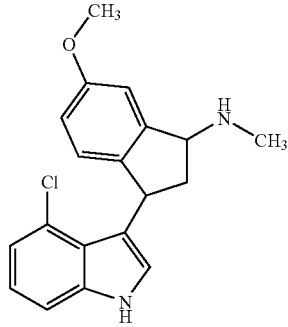

Example 13

Racemic cis-[3-(5,6-Difluoro-1H-indol-3-yl)-6-methoxy-indan-1-yl]-methyl-amine

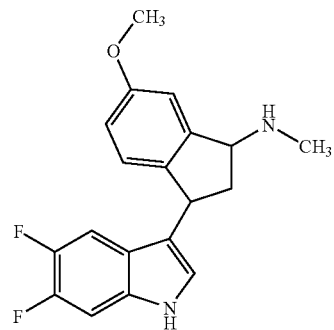

Example 14

Racemic cis-3-(6-Chloro-3-methylamino-indan-1-yl)-1H-indole-5-carbonitrile

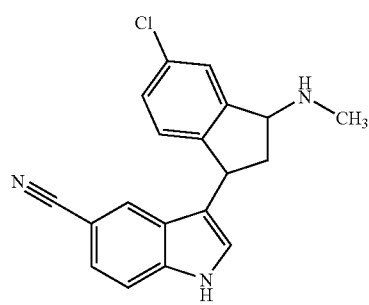

Example 15

Racemic cis-[5-Fluoro-3-(7-methyl-1H-indol-3-yl)-indan-1-yl]-methyl-amine

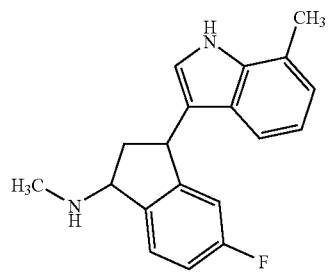

Example 16

Racemic cis-[3-(6-Bromo-1H-indol-3-yl)-5-fluoro-indan-1-yl]-methyl-amine

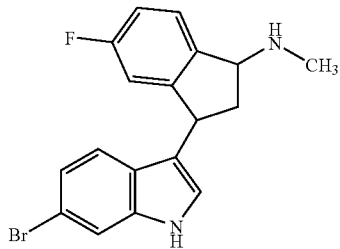

Example 23

Racemic cis-[3-(4,6-Difluoro-1H-indol-3-yl)-6-fluoro-indan-1-yl]-methyl-amine

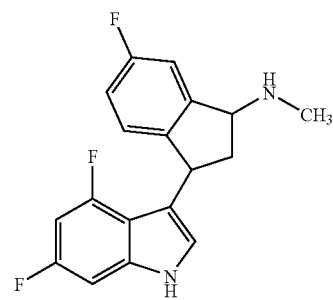

Example 24

Racemic cis-[5-Chloro-3-(5-fluoro-1H-indol-3-yl)-indan-1-yl]-methyl-amine

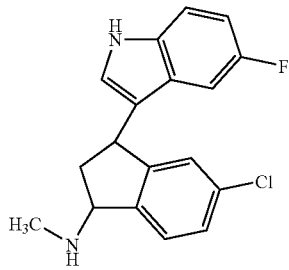

Synthesis of Example 19: cis-3-(3-Piperidin-1-yl-indan-1-yl)-1H-indole (Method 11)

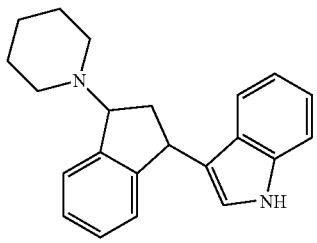

Sodium cyanoborohydride (61 mg; 0.97 mmol) was added to 3-(1H-indol-3-yl)-indan-1-one (200 mg; 0.81 mmol) and piperidine (344 mg; 4.05 mmol) in 3 mL methanol and 0.5 mL acetic acid. The reaction mixture was stirred 30 minutes at 150° C. under microwave irradiation using the Emry Optimizer™ instrument. The reaction mixture was poured into water and made basic with 27% aqueous NaOH. The mixture was extracted with ethyl acetate. The organic phase was dried over MgSO$_4$ and concentrated in vacuo. cis-3-(3-Piperidin-1-yl-indan-1-yl)-1H-indole was obtained after flash chromatography (ethyl acetate, heptane, triethylamine, silica gel).

The following compounds were synthesized in a similar way:

Example 20

Racemic cis-3-(3-Pyrrolidin-1-yl-indan-1-yl)-1H-indole

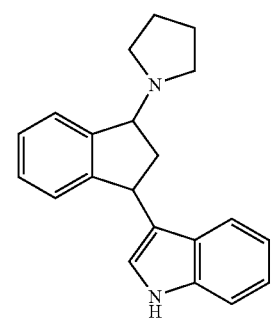

Example 21

Racemic cis-3-(3-Morpholin-4-yl-indan-1-yl)-1H-indole

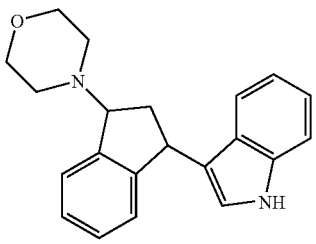

Synthesis of Example 10: [(1R,3R)-3-(1H-indol-3-yl)-indan-1-yl]-methyl-amine (Method 13)

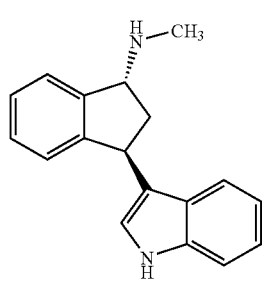
(Formula IX)

Dimethylbromoborane (1.77 mL, 1.05 equiv) (Synthesized according to Nöth, H., Vahrenkamp, H. *Journal of Organometallic Chemistry* 11(1968), 399-405) was added to 3-((1R,3R)-3-azido-indan-1-yl)-1-(toluene-4-sulfonyl)-1H-indole (17.3 mmol ) in 100 mL 1,2-dichloro-ethane under argon at 0° C. The reaction mixture was warmed to room temperature and stirred 2.5 hours. 1 mL Ethanol was added. The reaction mixture was extracted with ethyl acetate and 0.5N aqueous NaOH. The organic phase was washed with brine, dried over $MgSO_4$, concentrated in vacuo to give methyl-{(1R,3R)-3-[1-(toluene-4-sulfonyl)-1H-indol-3-yl]-indan-1-yl}-amine after flash chromatography (ethyl acetate, methanol, triethylamine, silica gel). Methyl-{(1R,3R)-3-[1-(toluene-4-sulfonyl)-1H-indol-3-yl]-indan-1-yl}-amine was dissolved in 8 mL acetone and 20 mL methanol. 8 mL 28% Aqueous NaOH was added and the reaction mixture was stirred in two portions at 120° C. for 10 minutes under microwave irradiation using the Emry Optimizer™ instrument. The reaction mixture was poured into 250 mL water and a precipitate was formed. Recrystallization gave 2.15 g [(1R,3R)-3-(1H-indol-3-yl)-indan-1-yl]-methyl-amine.

Chiral SFC: Method: Column: 250×4.6 mm Chiralcel OJ-H with 5 μM particles operated at room temperature. Chromatography was carried out using 30% of 0.1% (v/v) diethylamin in ethanol as modifier, a pressure of 20 MPa and a flow rate 3 ml/min. Detection at 230 nm. $RT_{major}$=2.40 min, $RT_{minor}$=2.93 min, 95.9% ee.

LC/MS: Method A: RT=1.63 min. UV-purity=98.28%, ELSD purity=99.61% $^1$H-NMR ($d_6$-DMSO): δ 2.35 (m, 5H), 4.17 (dd, J=3.8 Hz, 6.6 Hz, 1H), 4.75 (t, J=7.5 Hz, 1H), 6.90 (t, J=7.1 Hz, 1H), 7.00 (m, 3H), 7.14 (t, J=7.3 Hz, 1H), 7.19 (t, J=7.3 Hz, 1H), 7.26 (d, J=8.0 Hz, 1H) 7.34 (d, J=7.3 Hz, 1H), 7.38 (d, J=7.3 Hz, 1H), 10.80 (bs, 1H). $^{13}$C-NMR ($d_6$-DMSO): δ 34.2, 39.9, 41.3, 63.6, 111.9, 118.0, 118.5, 119.1, 121.3, 122.4, 124.8, 125.0, 126.4, 126.7, 127.6, 137.1, 145.3, 147.2.

The following compound was synthesized in a similar way:

Example 27

[(1R,3R)-3-(6-Methoxy-1H-indol-3-yl)-indan-1-yl]-methyl-amine

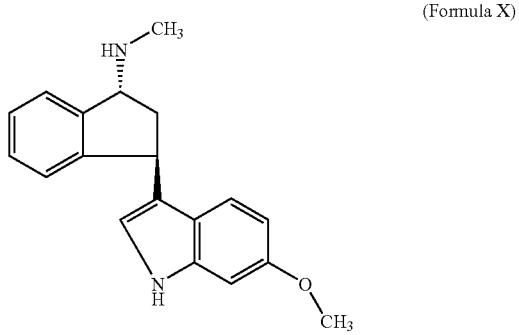
(Formula X)

LC/MS: Method A: RT=1.60 min. UV-purity=98.52%, ELSD purity 99.53% $^1$H-NMR ($CDCl_3$): δ 2.41 (ddd, J=3.8 Hz, 7.5 Hz, 12.8 Hz, 1H), 2.50 (t, J=6.8 Hz, 1H), 2.53 (s, 3H), 3.83 (s, 3H), 4.27 (dd, J=3.8 Hz, 6.8 Hz, 1H), 4.79 (t, J=7.5 Hz, 1H), 6.72 (m, 2H), 6.85 (s, 1H), 7.2 (m, 4H), 7.40 (d, J=7.3Hz, 1H), 7.82 (bs, 1H).

Synthesis of Example 25

Racemic trans-[6-Chloro-3-(5-methoxy-1H-indol-3-yl)-indan-1-yl]-methyl-amine (Method 13)

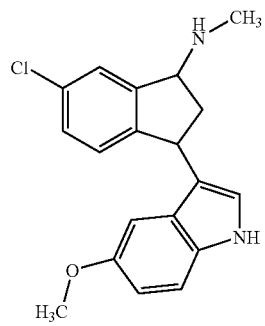

0.15 mmol Dimethylbromoborane (Synthesized according to Nöth, H., Vahrenkamp, H. *Journal of Organometallic Chemistry* 11(1968), 399-405) in 0.5 mL dry 1,2-dichloroethane was added to approximately 0.1 mmol [3-(3-Azido-6-chloro-indan-1-yl)-indol-1-yl]-phosphonic acid diphenyl ester in 2 mL dry 1,2-dichloroethane. The reaction mixture was stirred 3 hours at room temperature. The reaction was quenched by the addition of 1 mL 1 N NaOH and 1 mL brine. The mixture was extracted with ethyl acetate. The organic phase was concentrated in vacuo. The residue was treated with 3 mL 1M sodium methoxide in methanol for 3 h ar room temperature. 1 mL acetic acid was added and [6-Chloro-3-(1H-indol-3-yl)-indan-1-yl]-methyl-amine was isolated after preparative HPLC.

The following compounds were synthesized in a similar way:

Example 17

Racemic trans-[3-(6-Fluoro-1H-indol-3-yl)-indan-1-yl]-methyl-amine

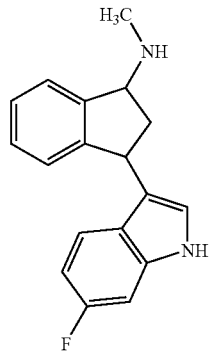

Example 18

Racemic trans-[3-(6-Methoxy-1H-indol-3-yl)-indan-1-yl]-methyl-amine

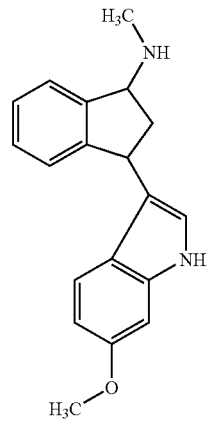

Example 22

Racemic trans-[3-(4-Chloro-1H-indol-3-yl)-6-fluoro-indan-1-yl]-methyl-amine

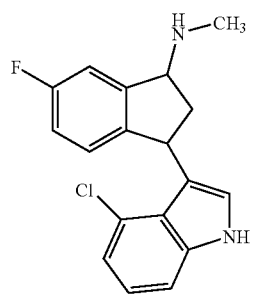

Synthesis of Example 26: [(1R,3R)-3-(5-chloro-1H-indol-3-yl)-indan-1-yl]-methyl-amine (Method 14)

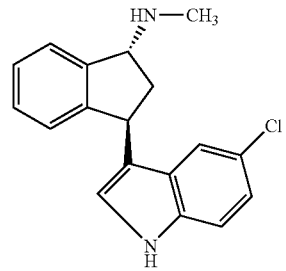

(Formula VIII)

0.73 g (1R,3R)-3-(5-chloro-1H-indol-3-yl)-indan-1-ylamine was suspended in 200 mL 1,2-dichloro-ethane, 100 mL water and 0.5 mL 9N NaOH. 0.25 mL Methyl chloroformate (1.2 equiv) and 50 mg Bu$_4$NBr were added. The reaction mixture was stirred 30 minutes at room temperature. The organic phase was dried over MgSO$_4$ and concentrated in vacuo to give 0.6 g [(1R,3R)-3-(5-chloro-1H-indol-3-yl)-indan-1-yl]-carbamic acid methyl ester. 0.6 g [(1R,3R)-3-(5-Chloro-1H-indol-3-yl)-indan-1-yl]-carbamic acid methyl ester was obtained after aqueous work up. [(1R,3R)-3-(5-Chloro-1H-indol-3-yl)-indan-1-yl]-carbamic acid methyl ester was dissolved in 250 mL dry THF and 0.6 g LiAlH$_4$ was added. The reaction mixture was refluxed for 2 hours. The reaction was quenched with 2 mL water, filtered and concentrated in vacuo to give an oil. The oil was dissolved in ethyl acetate and 350 mg [(1R,3R)-3-(5-chloro-1H-indol-3-yl)-indan-1-yl]-methyl-amine precipitated on standing at room temperature over night.

Chiral SFC: Method: Column: 250×4.6 mm Chiralcel AD-H with 5 μM particles operated at room temperature. Chromatography was carried out using 30% of 0.1% (v/v) diethylamin in ethanol as modifier, a pressure of 20 MPa and a flow rate 3 ml/min. Detection at 230 nm. RT$_{major}$=2.89 min, RT$_{minor}$=3.84 min, 88.6% ee.

LC/MS: Method C: RT=1.54 min. UV-purity=95.21%, ELSD purity=100% $^{13}$H-NMR (CDCl$_3$): δ 2.38-2.52 (m, 2H), 2.53 (s, 3H), 4.27 (dd, J=3.9 Hz, 6.6 Hz), 4.77 (t, J=7.4), 6.82 (s, 1H), 7.12 (dd, J=2.0 hZ, 8.5 Hz, 1H), 7.20-7.27 (m, 3H)7.37 (d, J=2.0 Hz), 7.42 (d, J=7.4 Hz), 8.16 (bs, 1H).

Chiral separation of racemic cis-3-(7-Fluoro-1H-indol-3-yl)-indan-1-yl-methyl-amine (Method 15)

20 g of racemic cis-3-(7-Fluoro-1H-indol-3-yl)-indan-1-yl-methyl-amine (from Method 10) was purified by chiral SFC to give 9.3 g of [(1S,3R)-3-(7-Fluoro-1H-indol-3-yl)-indan-1-yl]-methyl-amine with >99.5% ee and 9.5 g of [(1R,3S)-3-(7-Fluoro-1H-indol-3-yl)-indan-1-yl]-methyl-amine with >99.5% ee.

Preparative scale chiral SFC purification method: Column: Chiralcel OJ-H (2×25 cm) with 5 μM particles operated at 35° C. Chromatography was carried out using 35% of methanol with 0.1% (v/v) diethylamine as modifier in CO2 (100 bar) and a flow rate 50 ml/min.

Fractional crystallization of racemic cis-3-(7-Fluoro-1H-indol-3-yl)-indan-1-yl-methyl-amine with an optically active acid (Method 16)

To a solution of the racemate cis-3-(7-Fluoro-1H-indol-3-yl)-indan-1-yl-methyl-amine (409 mg/2ml EtOH) was added a solution of Di-p-toluoyl-D-tartaric acid (1 eq; 564 mg/2 ml Acetone). The mixture was heated to 50° C. and stirred for 15min. Evaporated the solvent and triturated with acetone (2 ml). The white solid (84% ee) was collected and stirred with 10 ml hot EtOH for 30 min. The remaining white solid was collected and converted to free base to give [(1S,3R)-3-(7-Fluoro-1H-indol-3-yl)-indan-1-yl]-methyl-amine (93% ee).

TABLE A

Measured molecular mass (M + H$^+$), measured HPLC-retention time (R$_t$, min) and UV- and ELSD- purities (%).

| Example No. | M + H$^+$ | R$_t$ (min.) | UV purity % | ELSD purity % | Method |
|---|---|---|---|---|---|
| 1 | 295.2 | 1.82 | 98.6 | 99.9 | A |
| 2 | 293.2 | 1.79 | 96.7 | 99.2 | A |
| 3 | 277.2 | 1.91 | 92.5 | 99.9 | A |
| 4 | 281.1 | 1.78 | 91.5 | 99.6 | A |
| 5 | 297.1 | 1.94 | 89.7 | 99.6 | A |
| 6 | 297.1 | 1.98 | 89.3 | 99.6 | A |
| 7 | 263.1 | 1.66 | 91.1 | 99.6 | A |
| 8 | 281.1 | 1.85 | 99.3 | 96.8 | A |
| 9 | 281.0 | 1.89 | 95.2 | 99.5 | A |
| 10 | 263.1 | 1.64 | 91.9 | 100.0 | A |
| 11 | 327.1 | 1.97 | 92.9 | 99.9 | A |
| 12 | 327.1 | 2.02 | 74.5 | 99.3 | A |
| 13 | 329.1 | 1.94 | 88.0 | 99.7 | A |
| 14 | 322.1 | 1.83 | 89.2 | 99.9 | A |
| 15 | 295.2 | 1.93 | 92.2 | 99.1 | A |
| 16 | 359.0 | 2.07 | 87.7 | 99.4 | A |
| 17 | 281.1 | 1.77 | 96.8 | 99.6 | A |
| 18 | 293.2 | 1.75 | 96.2 | 100.0 | A |
| 19 | 317.1 | 1.85 | 85.1 | 99.0 | A |
| 20 | 303.1 | 1.82 | 98.3 | 98.9 | A |
| 21 | 319.0 | 1.72 | 94.3 | 99.4 | A |
| 22 | 315.1 | 1.88 | 90.2 | 99.8 | A |
| 23 | 317.1 | 1.89 | 87.8 | 99.3 | A |
| 24 | 315.1 | 1.90 | 89.3 | 98.6 | A |
| 25 | 327.1 | 1.89 | 82.7 | 99.3 | A |
| 26 | 297.2 | 0.94 | 94.5 | 99.4 | B |
| 27 | 293.1 | 1.60 | 98.5 | 99.5 | A |

Transporter Inhibition Assays

Measurements of [$^3$H]-5-HT Uptake into Rat Cortical Synaptosomes

Whole brains from male Wistar rats (125-225 g), excluding cerebellum, are homogenized in 0.40 M sucrose supplemented with 1 mM nialamid with a glass/teflon homogenizer. The homogenate is centrifuged at 1000×g for 10 min at 4° C. The pellet is discarded and the supernatant is centrifuged at 40.000×g for 20 min. The final pellet is homogenized in assay buffer (0.5 mg original tissue/well). Test compounds (or buffer) and 10 nM [$^3$H]-5-HT are added to 96 well plates. Composition of assay buffer: 123 mM NaCl, 4.82 mM KCl, 0.973 mM CaCl$_2$, 1.12 mM MgSO$_4$, 12.66 mM Na$_2$HPO$_4$, 2.97 mM NaH$_2$PO$_4$, 0.162 mM EDTA, 2 g/l glucose and 0,2 g/l ascorbic acid. Buffer is oxygenated with 95% O$_2$/5% CO$_2$ for 10 min. The incubation is started by adding tissue to a final assay volume of 0.2 mL. After 15 min incubation with radio-ligand at 37 ° C., samples are filtered directly on Unifilter GF/C glass fiber filters (soaked for 30 min in 0.1% polyethylenimine) under vacuum and immediately washed with 1×0.2 ml assay buffer. Non-specific uptake is determined using citalopram (10 µM final concentration). Citalopram is included as reference in all experiments as dose-response curve.

Measurements of [$^3$H]Noradrenaline Uptake into Rat Cortical Synaptosomes

Fresh occipital-, temporal-og parietal cortex from male Wistar rats (125-225 g) are homogenized in 0.4M sucrose with a glass/teflon homogenizer. The homogenate is centrifuged at 1000×g for 10 min at 4° C. The pellet is discarded and the supernatant is centrifuged at 40.000×g for 20 min. The final pellet is homogenized in this assay buffer: 123 mM NaCl, 4.82 mM KCl, 0.973 mM CaCl$_2$, 1.12 mM MgSO$_4$, 12.66 mM Na$_2$HPO$_4$, 2.97 mM NaH$_2$PO$_4$, 0.162 mM EDTA, 2 g/l glucose and 0.2 g/l ascorbic acid (7.2 mg original tissue/mL=1 mg/140 µl). Buffer is oxygenated with 95% O$_2$/5% CO$_2$ for 10 min. Pellet is suspended in 140 volumes of assaybuffer. Tissue is mixed with test compounds and after 10 min pre-incubation, 10 nM [$^3$H]-noradrenaline is added to a final volume of 0.2 ml and the mixture is incubated for 15 min at 37° C. After 15 min incubation, samples are filtered directly on Unifilter GF/C glass fiber filters (soaked for 30 min in 0.1% polyethylenimine) under vacuum and immediately washed with 1×0.2 mL assay buffer.

Non-specific uptake is determined using talsupram (10 µM final concentration). Duloxetine is included as reference in all experiments as dose-response curve.

Measurements of [$^3$H]Dopamine Uptake into Rat Cortical Synaptosomes

Tissue preparation: male wistar rats (125-250 g) are sacrificed by decapitation and striatum quickly dissected out and placed in ice cold 0.40 M sucrose. The tissue is gently homogenised (glass teflon homogeniser) and the P2 fraction is obtained by centrifugation (1000 g, 10 minutes and 40000 g, 20 minutes, 4° C.) and suspended in 560 volumes of a modified Krebs-Ringer-phosphate buffer, pH 7.4.

Tissue 0,25 mg/well(140 µl) (original tissue) is mixed with test suspension. After 5 minutes pre-incubation at room temperature, 12.5 nM 3H-dopamine is added and the mixture is incubated for 5 minutes at room temperature. Final volume is 0.2 mL.

The incubation is terminated by filtering the samples under vacuum through Whatman GF/C filters with a wash of 1×0.2ml buffer. The filters are dried and appropriate scintillation fluid (Optiphase Supermix) is added. After storage for 2 hours in the dark the content of radioactivity is determined by liquid scintillation counting. Uptake is obtained by subtracting the non-specific binding and passive transport measured in the presence of 100 µM of benztropin. For determination of the inhibition of uptake ten concentrations of drugs covering 6 decades are used.

$^3$H-DA=3,4-(ring-2,5,6-$^3$H)dopamine hydrochloride from New England Nuclear, specific activity 30-50 Ci/mmol.

The following references are incorporated herein by reference in their entirety:

Hyttel, Biochem. Pharmacol. 1978, 27, 1063-1068;

Hyttel, Prog. Neuro-Psychopharmacol. & bil. Psychiat. 1982, 6, 277-295;

Hyttel & Larsen, Acta Pharmacol. Tox. 1985, 56, suppl. 1, 146-153.

As shown in Table 1, activity (IC$_{50}$) at the monoamine transporter for the compounds in the present invention was determined to be within the range of 0.1-200 nM.

TABLE 1

| Compound Activity at the Monoamine Transporter | | | |
|---|---|---|---|
| | 5-HTT (IC$_{50}$ nM) | DAT (IC$_{50}$ nM) | NAT (IC$_{50}$ nM) |
| Formula VI | * | * | * |
| Formula VII | * | * | * |
| Formula VIII | * | * | * |
| Formula IX | * | * | * |
| Formula X | * | * | * |
| Indatraline | * | * | * |
| Sertraline | * | * | * |

* 0.1–200 nM.
5-HTT Serotonin Transporter
DAT Dopamine Transporter
NAT Noradrenergic Transporter

What is claimed is:

1. A compound represented by the Formula I:

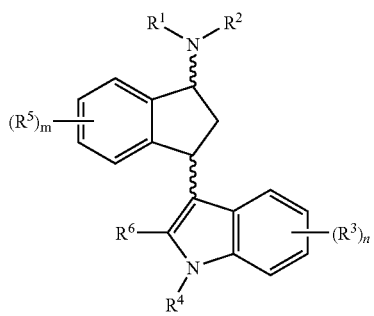

wherein

R$^1$ and R$^2$ are each independently hydrogen, C$_1$-C$_8$-straight or branched alkyl or C$_3$-C$_8$-cycloalkyl; or R$^1$ and R$^2$ and the nitrogen to which they are attached form azetidine, piperidine, pyrrolidine, azapane or morpholine;

each R$^3$ is independently hydrogen, C$_1$-C$_8$-straight or branched alkyl, C$_1$-C$_5$-alkoxy, C$_1$-C$_8$-straight or branched polyfluoroalkyl, halogen, cyano, hydroxyl, tetrazole -optionally substituted with methyl, or amino; or two R$^3$ groups on adjacent carbons combine together to form a methylenedioxy linker;

R$^4$ is hydrogen, C$_1$-C$_8$-straight or branched alkyl or C$_3$-C$_8$-cycloalkyl;

each R$^5$ is hydrogen, halogen C$_1$-C$_5$-alkoxy, C$_1$-C$_8$-straight or branched alkyl, C$_1$-C$_8$-straight or branched polyfluoroalkyl, cyano, or hydroxyl;

m is an integer from 1 to 4 inclusive;

n is an integer from 1 to 4 inclusive; and

R$^6$ is hydrogen, C$_1$-C$_8$-straight or branched alkyl or phenyl; or a pharmaceutically acceptable salt thereof.

2. The compound of claim 1, wherein the compound is the cis isomer.

3. The compound of claim 1, wherein the compound is the trans isomer.

4. The compound according to claim 1 selected from the group consisting of Formula II-V:

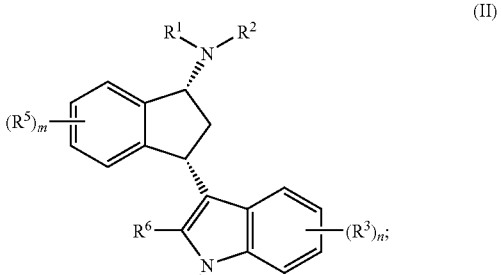

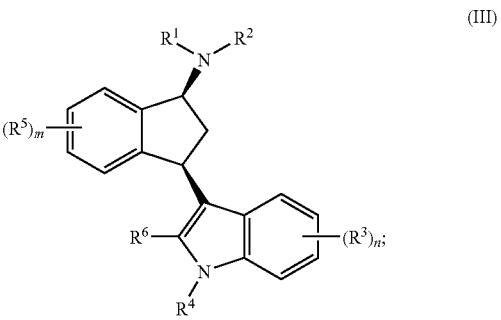

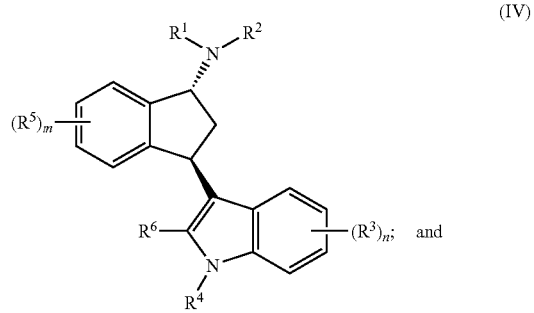

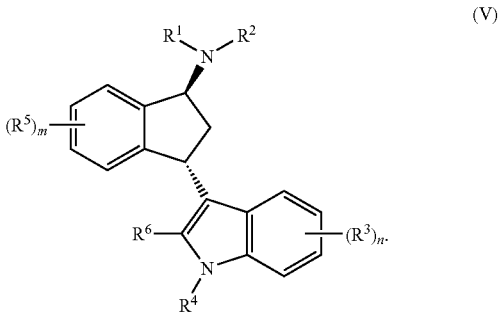

5. The compound of Formula II, III, IV or V according to claim 4, wherein R$^1$ is hydrogen.

6. The compound of claim 5, wherein R$^2$ is methyl.

7. The compound of claim 6, wherein R$^4$ is hydrogen.

8. The compound of claim 7, wherein R$^3$ is selected form the group consisting of hydrogen, halogen, and methoxy.

9. The compound of claim 8, wherein R$^3$ is a hydrogen or halogen.

10. The compound of claim 9, wherein the halogen is fluorine or chlorine.

11. The compound of claim 10, wherein R$^5$ and R$^6$ are hydrogen.

12. A compound selected from the group consisting of:
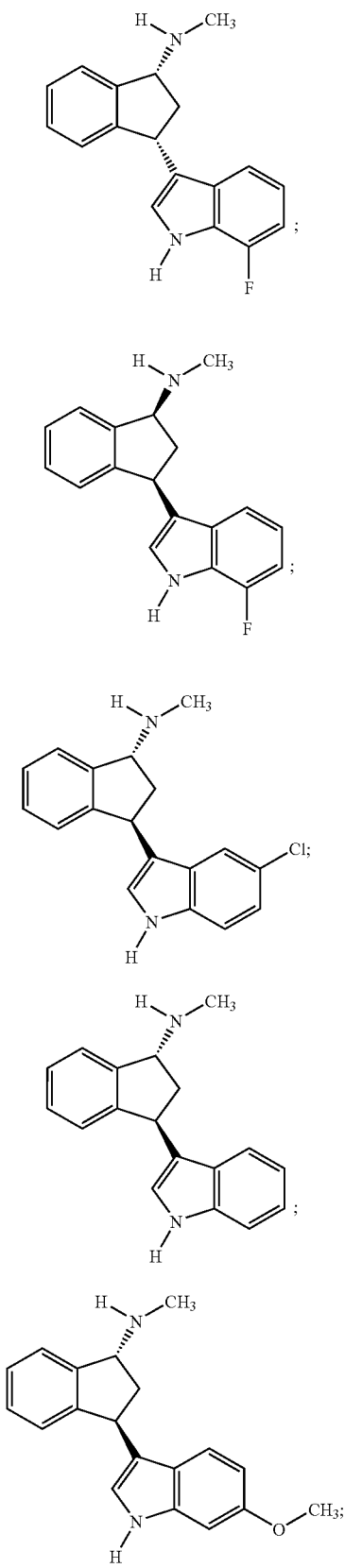
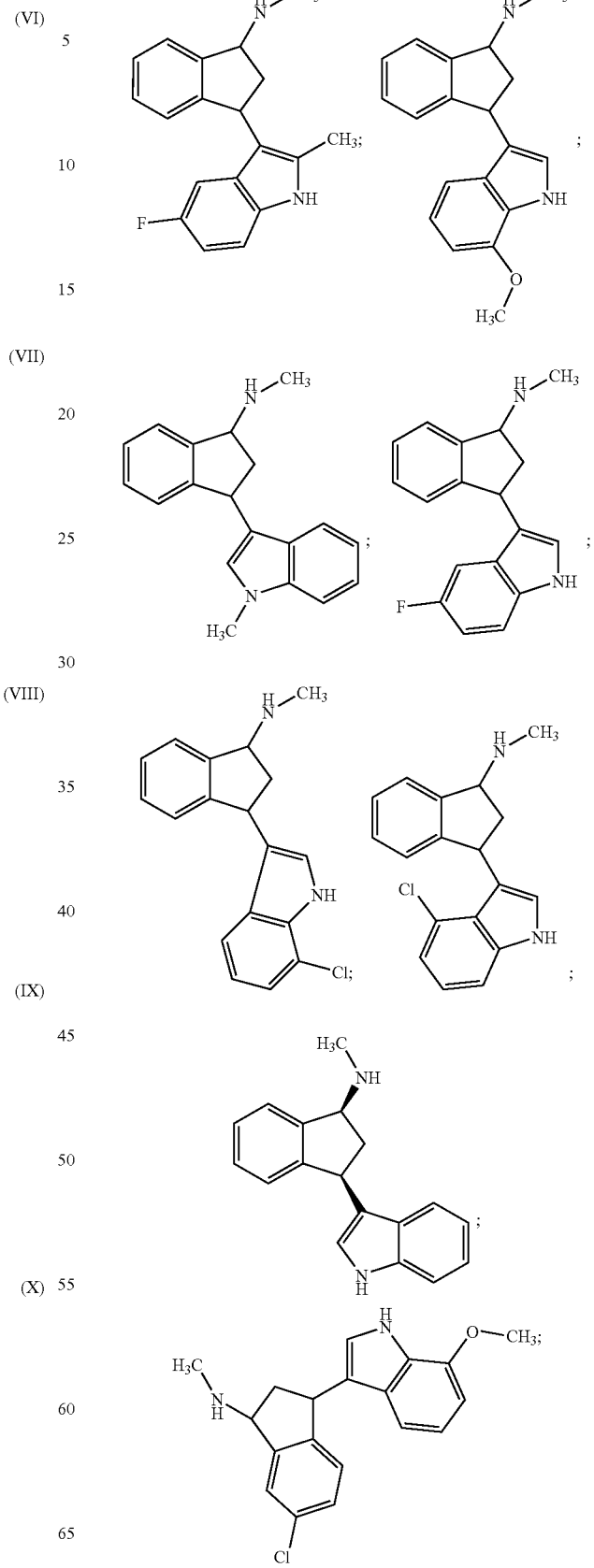

-continued
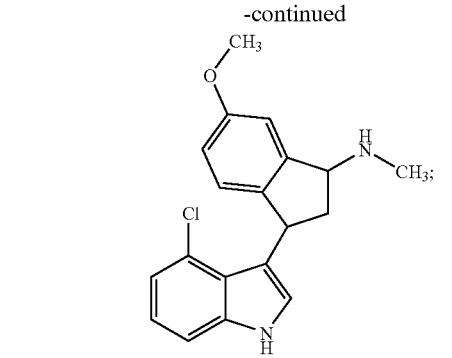
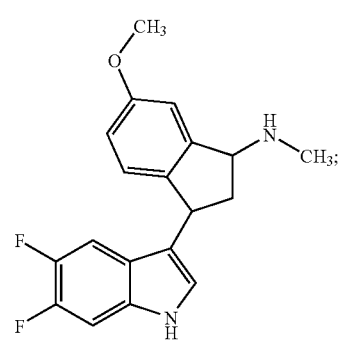
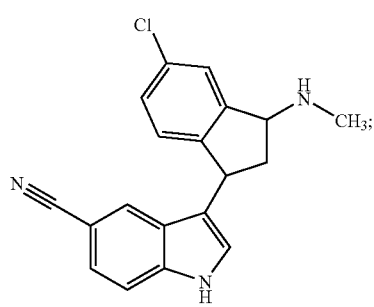
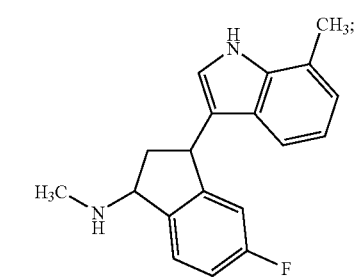
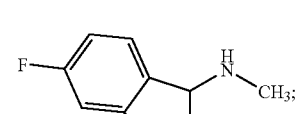
-continued
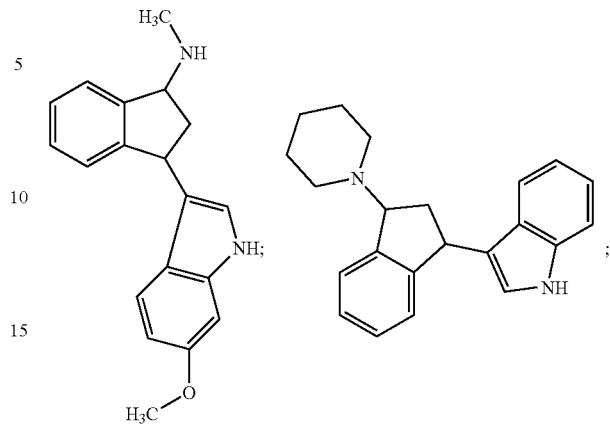
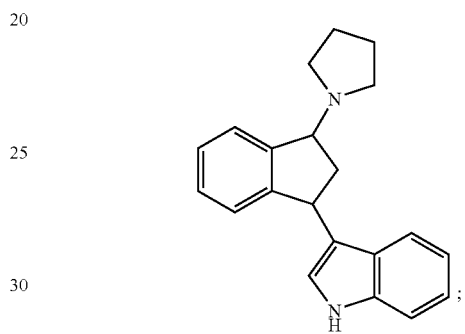
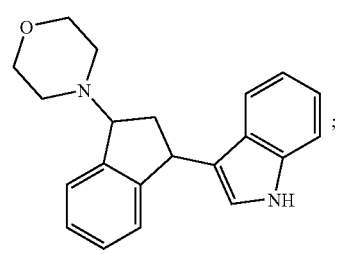
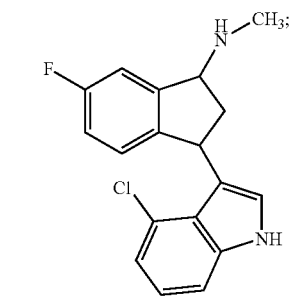
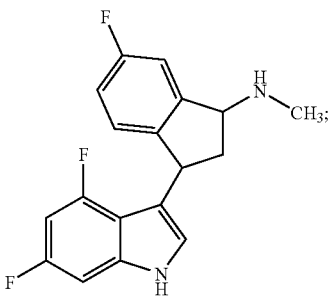

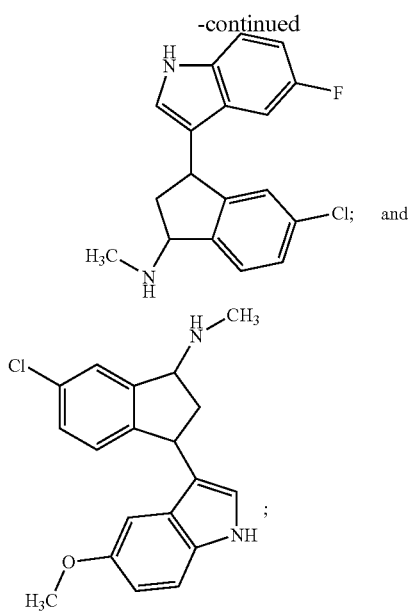

or a pharmaceutically acceptable salt thereof.

13. A pharmaceutical composition comprising a therapeutically effective amount of the compound of any one of claim 1 and a pharmaceutically acceptable carrier.

14. A method for the treatment of depressive disorders, anxiety disorders, pain disorders, and attention deficit hyperactivity disorder (ADHD) in a patient in need thereof, comprising administering to the patient a therapeutically effective amount of a compound of claim 1.

15. The method of claim 14, wherein the depressive disorder to be treated is selected from the group consisting of major depressive disorder, melancholia, postnatal depression, dysthymia, depression associated with bipolar disorder, depression associated with Alzheimer's disease, depression associated with psychosis, and depression associated with Parkinson's disease.

16. The method of claim 14, wherein the anxiety disorder to be treated is selected from the group consisting of general anxiety disorder, social anxiety disorder, post traumatic stress disorder, obsessive compulsive disorder, panic disorder, panic attacks, specific phobias, social phobia and agoraphobia.

17. The method of claim 14, wherein the pain disorder to be treated is selected from the group consisting of fibromyaglia syndrome (FMS), overall pain, backpain, shoulder pain, headache, pain while awake and pain during daily activities.

18. A pharmaceutical composition comprising a therapeutically effective amount of the compound of claim 12 and a pharmaceutically acceptable carrier.

19. A method for the treatment of depressive disorders, anxiety disorders, pain disorders, and attention deficit hyperactivity disorder (ADHD) in a patient in need thereof, comprising administering to the patient a therapeutically effective amount of a compound of claim 12.

20. The method of claim 19, wherein the depressive disorder to be treated is selected from the group consisting of major depressive disorder, melancholia, postnatal depression, dysthymia, depression associated with bipolar disorder, depression associated with Alzheimer's disease, depression associated with psychosis, and depression associated with Parkinson's disease.

21. The method of claim 19, wherein the anxiety disorder to be treated is selected from the group consisting of general anxiety disorder, social anxiety disorder, post traumatic stress disorder, obsessive compulsive disorder, panic disorder, panic attacks, specific phobias, social phobia and agoraphobia.

22. The method of claim 19, wherein the pain disorder to be treated is selected from the group consisting of fibromyaglia syndrome (FMS), overall pain, backpain, shoulder pain, headache, pain while awake and pain during daily activities.

* * * * *